United States Patent
Houghton et al.

(10) Patent No.: US 12,116,562 B1
(45) Date of Patent: Oct. 15, 2024

(54) INTEGRATED SYSTEM FOR THE AUTOMATED PASSAGING OF ANCHORAGE DEPENDENT CELL CULTURES

(71) Applicant: Unicorn Biotechnologies Ltd., Sheffield (GB)

(72) Inventors: Albert William Houghton, Sheffield (GB); George Leonard Freeman, Knaresborough (GB); Carl Heimann, Sheffield (GB); Jakub Jasik, Sheffield (GB); Adam Mitchell, Sheffield (GB); Poppy Josephine Culshaw, Sheffield (GB); Adam Glen, Sheffield (GB)

(73) Assignee: Unicorn Biotechnologies Ltd., Sheffield (GB)

( * ) Notice: Subject to any disclaimer, the term of this patent is extended or adjusted under 35 U.S.C. 154(b) by 0 days.

(21) Appl. No.: 18/542,617

(22) Filed: Dec. 16, 2023

(51) Int. Cl.
  *C12M 1/36* (2006.01)
  *C12M 1/00* (2006.01)
  *C12M 3/00* (2006.01)

(52) U.S. Cl.
  CPC ............ *C12M 41/48* (2013.01); *C12M 23/42* (2013.01); *C12M 23/50* (2013.01); *C12M 29/00* (2013.01)

(58) Field of Classification Search
  CPC ...... C12M 41/48; C12M 23/42; C12M 23/50; C12M 29/00
  See application file for complete search history.

(56) References Cited

U.S. PATENT DOCUMENTS

| | | | | |
|---|---|---|---|---|
| 3,847,749 A | * | 11/1974 | Smith | C12M 29/00 435/308.1 |
| 4,844,872 A | * | 7/1989 | Geiselman | G01N 35/085 422/537 |
| 4,848,722 A | * | 7/1989 | Webster | F16K 11/022 137/884 |
| 4,852,851 A | * | 8/1989 | Webster | F16K 11/022 137/884 |
| 5,265,822 A | * | 11/1993 | Shober, Jr. | B65H 75/2281 242/388.2 |
| 6,066,497 A | * | 5/2000 | Powell | C12M 29/04 435/298.2 |

(Continued)

*Primary Examiner* — William H. Beisner
*Assistant Examiner* — Danielle B Henkel
(74) *Attorney, Agent, or Firm* — Eric P. Mirabel, JD, LLM

(57) ABSTRACT

Disclosed is a system for automating passaging of anchorage dependent or adherent mammalian cells, having a fluid distribution cartridge where fluid channels each has an associated pneumatically controlled valve, and the valves can be selectively opened and closed to allow fluid which is pumped into channels in the cartridge to be selectively passed or interrupted. The channels are connected with a series of vessels each held in a housing structure, and a first frame rests on a surface and a second frame is attached with the first frame such that the second frame can tilt on a first axis with respect to the first frame, and the housing is attached to the second frame such that the housing can tilt on a second axis with respect to the second frame, and wherein the second axis is orthogonal to the first axis. A digital system that controls selective opening and closing of the valves by controlling the pressurized air provided to the valves, and also controls the movement of the frames and housing under feedback from the leveling system.

19 Claims, 20 Drawing Sheets

(56) References Cited

U.S. PATENT DOCUMENTS

| | | | | |
|---|---|---|---|---|
| 6,712,963 | B2* | 3/2004 | Schick | B01D 61/147 |
| | | | | 210/257.2 |
| 7,001,513 | B2* | 2/2006 | Bell | A61M 1/02 |
| | | | | 210/198.2 |
| 7,846,335 | B2* | 12/2010 | Bisschops | G01N 30/20 |
| | | | | 210/656 |
| 9,283,521 | B2* | 3/2016 | Schick | B01D 61/18 |
| 11,713,440 | B2* | 8/2023 | Horii | C12M 27/14 |
| | | | | 435/289.1 |
| 11,903,710 | B2* | 2/2024 | Bullington | A61B 5/150221 |
| 2002/0045252 | A1* | 4/2002 | Yamashita | C12M 25/00 |
| | | | | 435/395 |
| 2002/0146817 | A1* | 10/2002 | Cannon | C12M 23/48 |
| | | | | 435/325 |
| 2003/0054335 | A1* | 3/2003 | Taya | C12M 41/36 |
| | | | | 435/325 |
| 2007/0065933 | A1* | 3/2007 | Esser | C12M 23/48 |
| | | | | 435/286.6 |
| 2010/0043891 | A1* | 2/2010 | Wilke | F16J 15/3236 |
| | | | | 137/484.2 |
| 2018/0282682 | A1* | 10/2018 | Pebay | C12M 41/48 |
| 2020/0232576 | A1* | 7/2020 | Gebauer | B01D 29/90 |
| 2021/0207073 | A1* | 7/2021 | Tanabe | C12M 41/46 |
| 2021/0278427 | A1* | 9/2021 | Ogg | B01L 3/502738 |
| 2021/0284948 | A1* | 9/2021 | Hauwaerts | A61K 39/464499 |
| 2021/0317399 | A1* | 10/2021 | Nazareth | C12M 41/48 |
| 2021/0340486 | A1* | 11/2021 | Andrews | C12M 23/44 |

\* cited by examiner

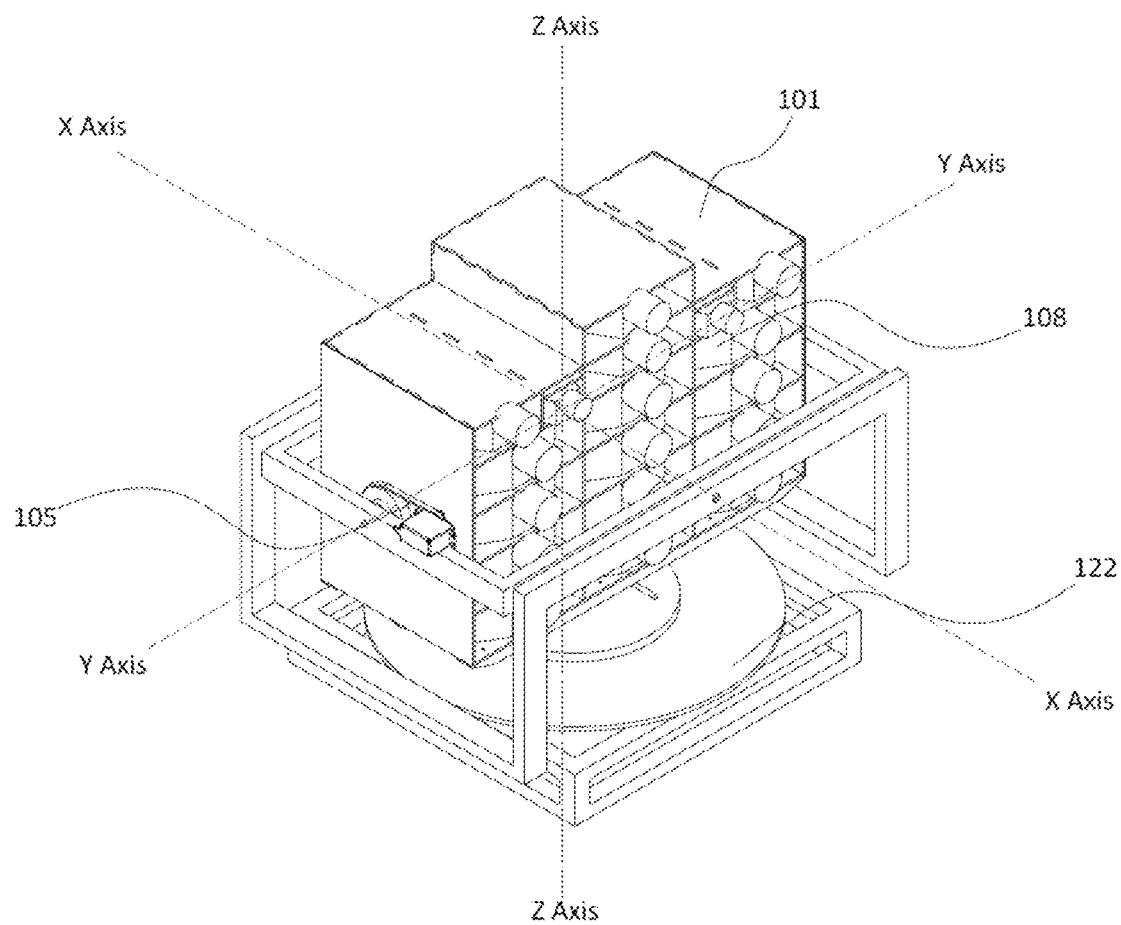

INTEGRATED SYSTEM FOR THE AUTOMATED PASSAGING OF ANCHORAGE DEPENDENT CELL CULTURES

BACKGROUND

There is increasing demand for the production of living cell-based products across a range of industries. In particular, there is increasing uptake of regenerative medicines including cell and stem cell-based therapeutic intervention and interest in cultivated meat. Both require the production of significant quantities of living cells, particularly stem cells and their differentiated progeny.

Currently, the process of manufacturing cells, known as cell culture, contains many manual processes that require a highly trained technical operator to complete. As such, the scaling up of cell culture manufacturing using current processes struggles with the required scale, cost-effectiveness, repeatability, and product quality that the market demands of cell culture-based products and therapies.

Many cell types, particularly stem cells, proliferate when adhered to a surface, and are known as adherent or anchorage-dependent cells. The process of manufacturing adherent cells involves seeding cells onto a surface that the cells can adhere to. Expanding the cells, where a small number of starting cells grows to a larger number of cells. And passaging where-once the cells are confluent, or have expanded to take up a predetermined percentage of the total available surface area of a cell culture vessel-cells are removed, usually using enzymatic dissociation methods, put into a suspension and then re-seeded into larger or multiple new cell culture vessels.

Adherent cells are particularly challenging to culture as the gold standard for culturing and manufacturing these cells, particularly when performing technically complex process steps such as passaging, is to utilise highly skilled, technical operators to manually perform these processes. Manual processes, however, are inherently variable and cannot reliably or economically scale to meet the needs of commercial production.

Automation is needed to reduce the cost of goods for manufacturing to enable mass market access for new therapeutic interventions and products based on stem cells or other adherent cell types. Automation of adherent cell culture then, including key process steps such as passaging, is crucial to enable industrial-scale manufacture of adherent cells, including stem cells either in a pluripotent state or to be processed into their differentiated progeny.

Systems to automate the culture of adherent cells have been described since the mid-20th century. Kunitake et. al., 1997 (DOI: 10.1016/s0168-1656(96)01654-9) describe a method for using roller bottles to expand adherent mammalian cells for use in biologics production, e.g. antibody or vaccine manufacture. However, this and similar approaches do not allow for the passaging of adherent cells between cell culture vessels.

The demand for treatments and therapeutic interventions for degenerative diseases of which stem cell-based therapies and cell therapy and regenerative medicine products more broadly can address, has increased dramatically in recent years. Attempts have been made to develop new systems and instrumentation to enable the automated passaging of adherent cells, with the goal of developing a method for scalable adherent cell manufacturing.

Several commercial systems have been brought to market to attempt the automation of adherent cell culture manufacturing, including the passaging steps (see the Automation Partnership Biosystems (TAP Biosystems), now part of Sartorius AG). However, these systems are expensive, difficult to adapt cell culture manufacturing processes to, and have high process variability when passaging of adherent cells.

To solve this challenge, more recent systems for automating adherent cell culture have been developed by using an integration system. Consisting generally of a robotic arm or manipulation device capable of moving labware which is then integrated with liquid handling and pipetting robots, microscopes, semi-automated incubators etc. into a single manufacturing workflow.

US Publication Nos. 20180282682A1 and 2021/0317399 (both incorporated by reference) disclose methods for using multi-instrument systems, leveraging a pipetting robot or fluid handling machine and robotic manipulators or arms, to passage adherent cells. However, these approaches are limited to using inherently low throughput labware, commonly referred to as well-plate, in their processes, and require multiple, expensive instruments for implementation. While suitable for research and development applications, these approaches cannot be reliably scaled up at economically viable price points to meet the demands of commercial adherent cell manufacturing.

To meet growing market demand, a new paradigm for adherent cell manufacturing systems is needed where the fundamental process steps of adherent cell culture, agitation and fluid exchange, are mechanized, automated and implemented in a single closed instrument. Furthermore, this instrument must be compatible with larger—e.g. physically larger cell culture vessels with enough surface area to support the culture of cells needed for commercial applications.

Larger cell culture vessels are not compatible with existing pipetting robots used for fluid exchange, as they require handling, levelling and sufficient fluid exchange during liquid exchange that exceeds the capabilities of most commercially available robotic manipulation systems. To solve this problem a new fluidics-based system for liquid handling is needed.

Fluidic control systems have been described in the literature, and several commercially available cell manufacturing systems for suspension cell culture utilise fluidic exchange and control systems (see the CliniMACS Prodigy™ Platform system marketed by Miltenyi Biotec). However, these fluid control systems depend on networks or manifolds of single-use tubing and sterile connections. Before each production run, every piece of tubing, and all of the connections between tubing and pumps, valves, reagent stores, waste vessels and cell culture vessels, must be replaced, re-made and certified to be sterile. This is an expensive and time-consuming process. Furthermore, when an existing fluidic management system is applied to adherent cell culture implementing tubing based fluidic management systems leads to complicated and expensive assembly, and long downtimes during tubing changes.

To make fluidic control viable for automating adherent cell culture, a novel fluidic control system is needed which reduces, or mitigates altogether, the need for extensive single-use tubing. This goal can be met with a cartridge-based fluid handling system, where input and output tubing, valves, and fluid routing can all be accomplished using a control cartridge with multiple valves, allowing fluid flow to different vessels and receptacles. This will drastically reduce the amount of tubing needed to complete a system run, and simplify the system set up. A reliable system for culturing is also needed, where the vessels can be oriented through specified tilts and movements, to optimize the cell growth.

SUMMARY

An automated cell culture system described herein includes a cartridge having a flexible membrane clamped between two blocks, capable of blocking integral fluid channels in the cartridge and forming the membrane in a series of independent pneumatically controlled valves. The integral fluid channels eliminate the need for tubing within the cartridge. Several pneumatically actuated diaphragm-type valves inside the cartridge can be used to direct fluid flow between vessels and receptacles in an automated manner, such that cell culture manufacturing process steps are carried out as desired for growing and manufacturing different cell types in different vessels and drawing fluids in and out from different receptacles.

The fluid flow to and from the cartridge can be powered by an external pump connected to the system, or an internal diaphragm-style pump. Another embodiment of the cartridge could also use the diaphragm valves for pumping by actuating them in a certain sequence to distribute small volumes of fluids within the system. Integrating valves and pumps into the cartridge helps in reducing the system's size and setup time. After installing the cartridge, only the appropriate input and output tubing is connected to the cartridge ports. Making and re-making numerous internal tubing connections, as in existing tubed manifolds, are not required.

Additionally, housing for vessels moveable through a plurality of axes is used to house and manipulate cell culture vessels, to allow reagents, cell culture media and cell suspensions in the vessels to be positioned or moved as desired, to optimize cell growth in the vessels. The housing is mounted in two or more nested frames, which preferably independently allow precise tilting and movement of the housing in two or more orthogonal axes. The frames are controlled by mechanical actuators, such as servo motors, which are in turn controlled by feedback from level sensors to allow the frames to control the tilt and movement of the housing in at least two axes, and therefore to control the fluid position and movement within the vessels.

Thus, the fluid can be pooled at precise locations within the vessels to aid cell culture steps such as filling and draining reagents, expanding or growing cells, performing cell culture and differentiation manufacturing protocols or passaging cells. The fluid motions which can be provided include rocking back and forth, side to side, and swirling, by applying a circular motion on the frames. These fluid motions aid the generation of homogenous cell suspensions, cell seeding distribution, mixing of reagents, and agitation of cells accomplished during the passaging process between the vessels.

Combining, the integrated pump, the fluid distribution cartridge, and the mechanical actuation system allows manual cell culture steps to be replicated in an automated manner which allows improvements in product quality, saves cost, and allows easier scale-up of cell manufacturing. This represents a novel mechanical and system design, and method for the automation of adherent cell culture workflows, particularly passaging.

BRIEF DESCRIPTION OF DRAWINGS

FIG. 21 is a perspective view of an embodiment of a multi-axis rocker system with oscillation about three axes.

DETAILED DESCRIPTION

Figure 1:
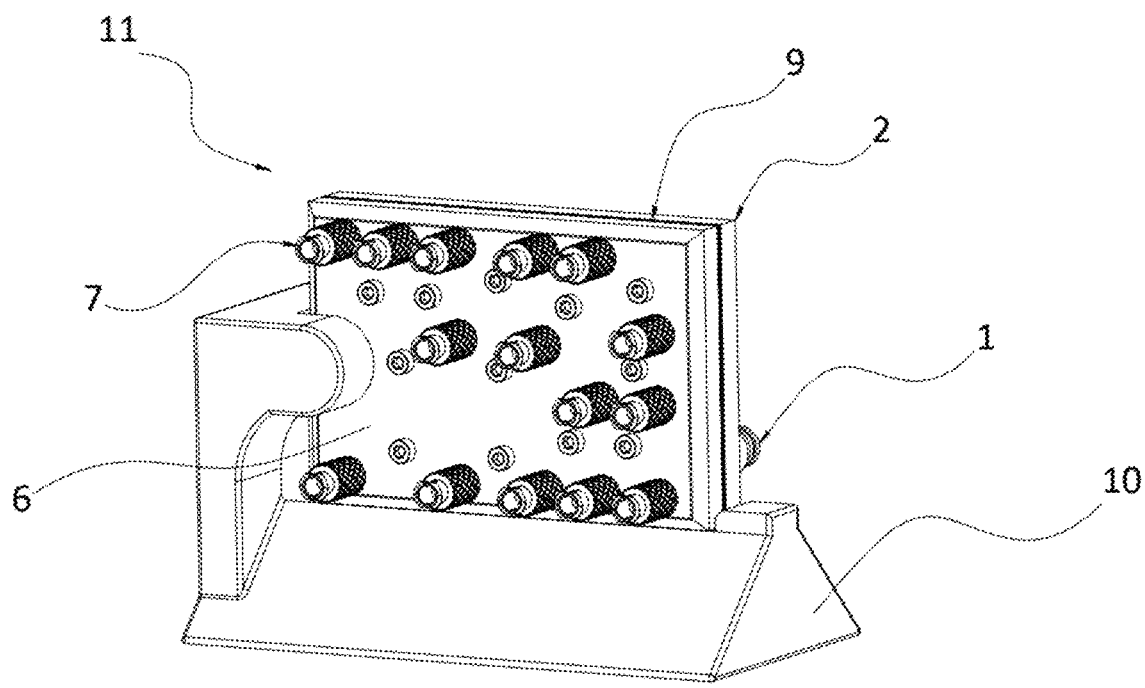
FIG. 1 is an elevational view of an assembled cartridge held in a stand, with fluidic connectors visible on one side.
Figure 2:
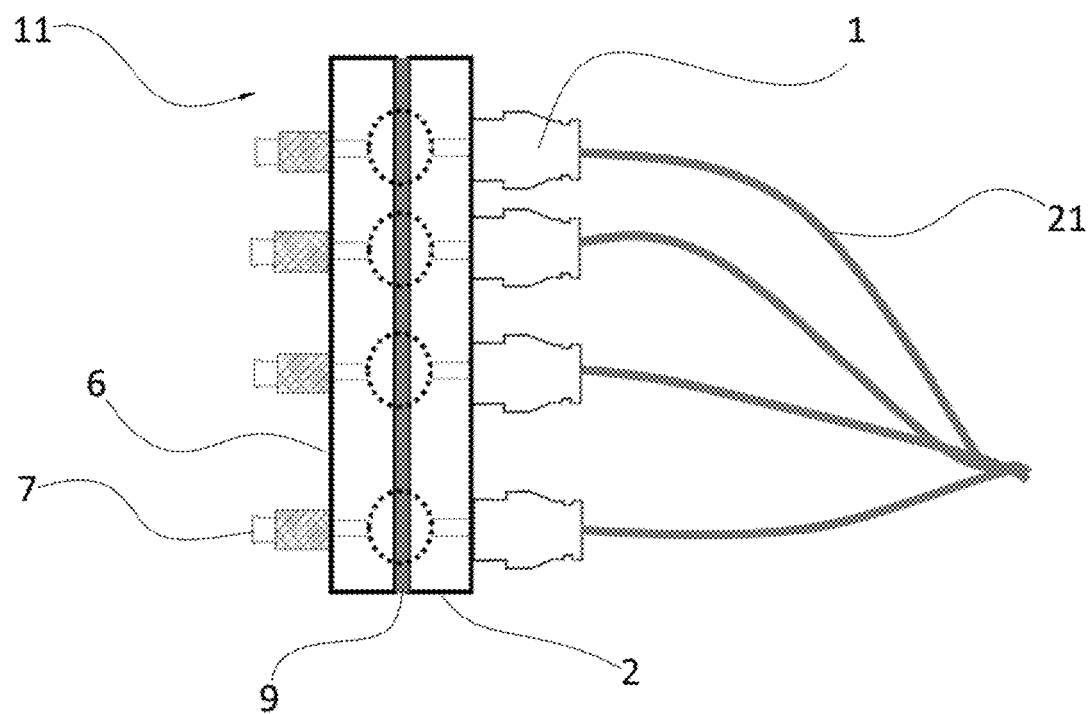
FIG. 2 is a side view of the assembled cartridge of FIG. 1, schematically depicting some components.

The disclosed invention includes an integrated and fully automated cell manufacturing system that facilitate the passaging of anchorage-dependent cells, which includes two primary subsystems: an automated, pneumatically controlled fluid exchange cartridge and a mechanical multi-axis rocker for cell culture vessel rocking and positioning.

The cartridge has a series of fluidic channels where fluid passage is controlled by pneumatically actuated valves to create a fluid handling system that allows cell suspensions and reagents to be accurately dispensed and removed from cell culture vessels, and/or transferred between various cell culture vessels and other receptacles. The cartridge facilitates the complex operations required for cell passaging among multiple cell culture vessels and other receptacles, as needed to optimize cell growth, especially for adherent cells.

The multi-axis rocker is under electro-mechanical control and allows the automation of adherent cell culture processes by oscillating in specified motions or providing specified positioning of cell culture vessels. The device provides for fluids to be accurately put through different motions within the culture vessels to aid cell culture steps—e.g. homogenously seeding cell suspensions and evenly applying dissociation reagents to ensure optimal harvesting and seeding of adherent cells during the passaging process.

Cartridge

Referring to connector 2, a cartridge 11 is formed of front side 6 and back side 2, with a membrane 9 sandwiched between sides 6 and 2. Frontal fluidic connectors 7 provide access from fluid channels 13 (See FIG. 3) within the front side of cartridge 6 to fluidic tubing. The tubing feeding fluid to frontal connectors 7 is not shown. The pressurized air is supplied via pneumatic tubing 21 connected to pneumatic connectors 1 attached to rear side 2. Cartridge 11 resides in a holder 10.

The fluidic connectors 7 are inserted into fluidic ports 16 inside the front side 6. See FIG. 13A. The pneumatic connectors 1 are screwed into threaded pressure ports 14. Pressure ports 14 provide access to membrane 9 which rests between the mated hemispherical domes 8. See FIGS. 13A and 13B.

The membrane 9 is a flexible elastic or polymeric sheet that is actuated to close and open valves on the fluid paths. One embodiment of this could be made of silicone but other types of flexible materials are also possible. In terms of manufacturing, it could be cut by hand, die cut, or cut via a CNC machine (laser, waterjet, or other).

Figure 32:
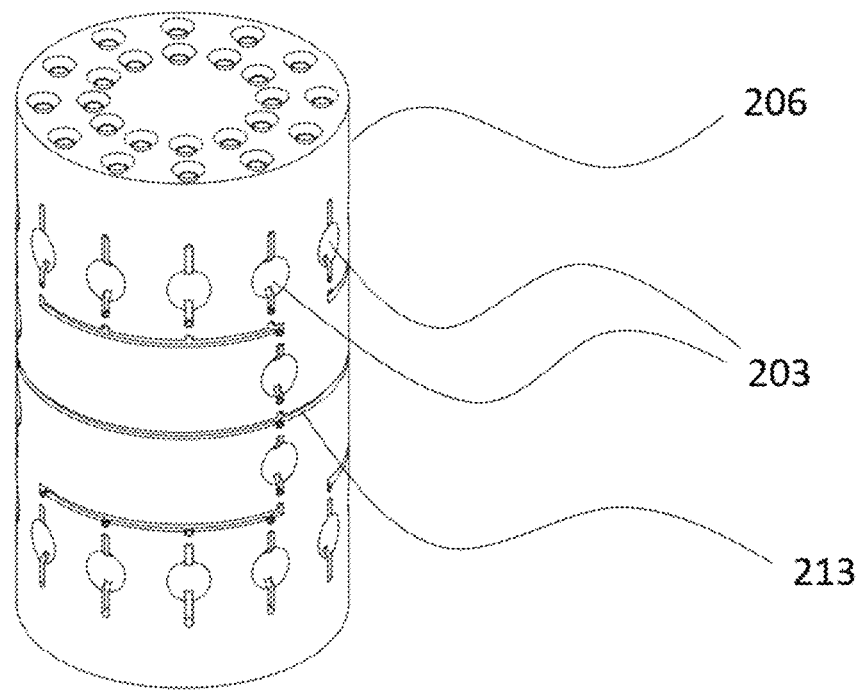
FIG. 32 is a perspective view of a cylindrical embodiment of the cartridge front side 206 of the invention, without connectors in place.
Figure 33:
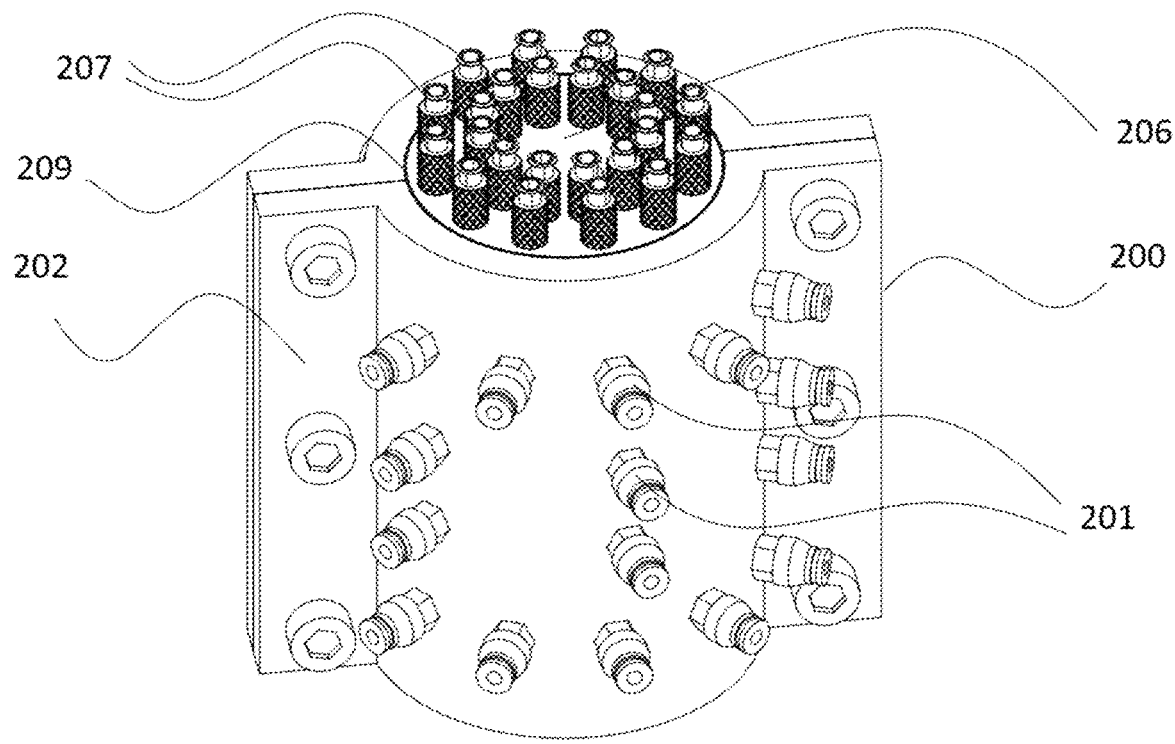
FIG. 33 is a perspective cartridge assembly 200 consisting of the front side 206 of FIG. 32 and the rear side 202 clamped together with a membrane 209 in between them. The assembled unit has pneumatic connectors 201 and fluidic connectors 207 in place.

Front side 6 and backside 2, with membrane 9 between, are held together with fasteners or adhesives that provide sufficient uniform compression to seal around the fluidic channels and the valves 3. In some embodiments, one could bond the membrane 9 to front side 6, or stretch it over the front side. Cartridge 11 could also have different shapes, including cylindrical, in other embodiments (see FIGS. 32 and 33, showing cylindrical embodiment 200 with front side 206, rear side 202, valves 203, connectors 201 and 207, and channels 213).

Figure 3:
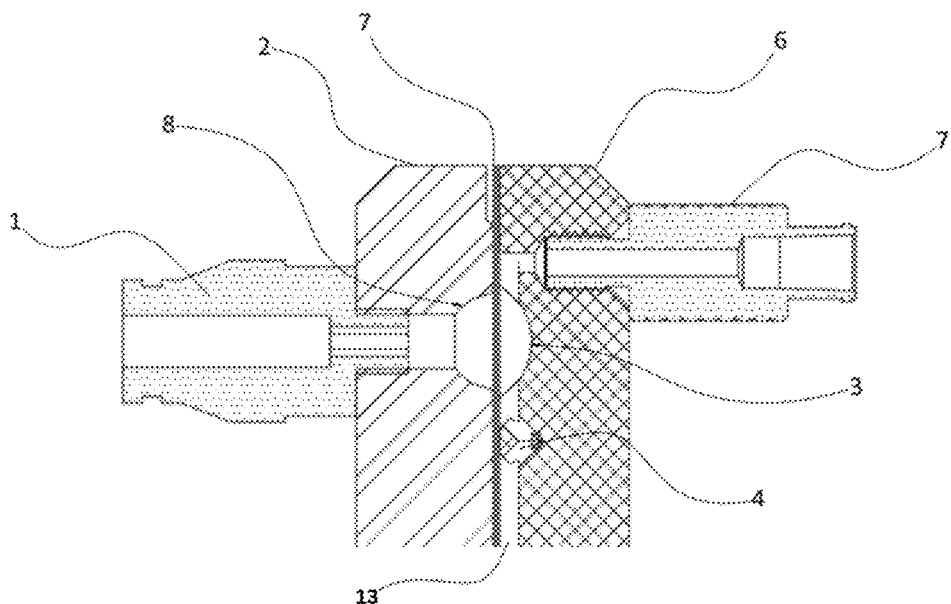
FIG. 3 is a cross-section view of the cartridge of FIG. 1, showing fluidic connectors, fluid valving and pneumatic connectors.

Referring to FIG. 3, it can be seen that fluid, that travels in the front side 6 of cartridge 11, can move along channel 13 through valve 3 to fluidic connector 7. When pressurized air is applied through rear connectors 1, it passes to hemispherical chamber 8 causing membrane 9 to move to the right and block fluid passage through valve 3. The dome-like valves 3 are formed in part by semi-hemispherical recesses 8 in front side 6. Their exact shape can change depending on end requirements. For example, their aspect ratio could change so they are more elliptical rather than circular, or their depth could change.

Figure 6:
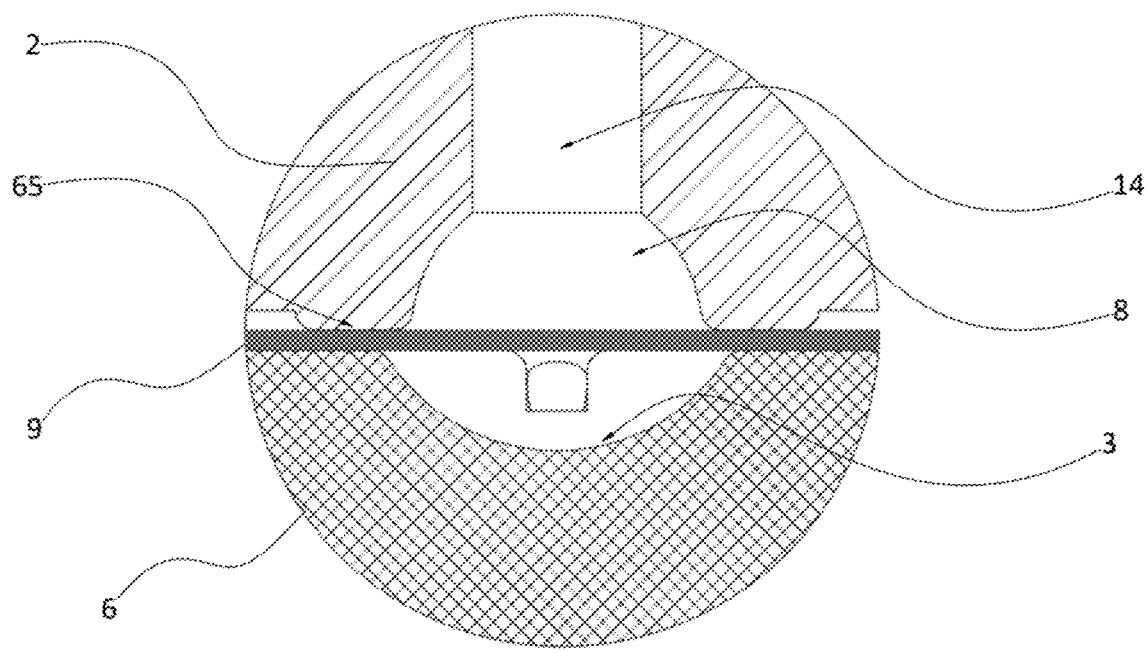
FIG. 6 is a close-up cross-section of the cartridge in FIG. 3, showing the fluidic valve and its components in its neutral position
Figure 11:
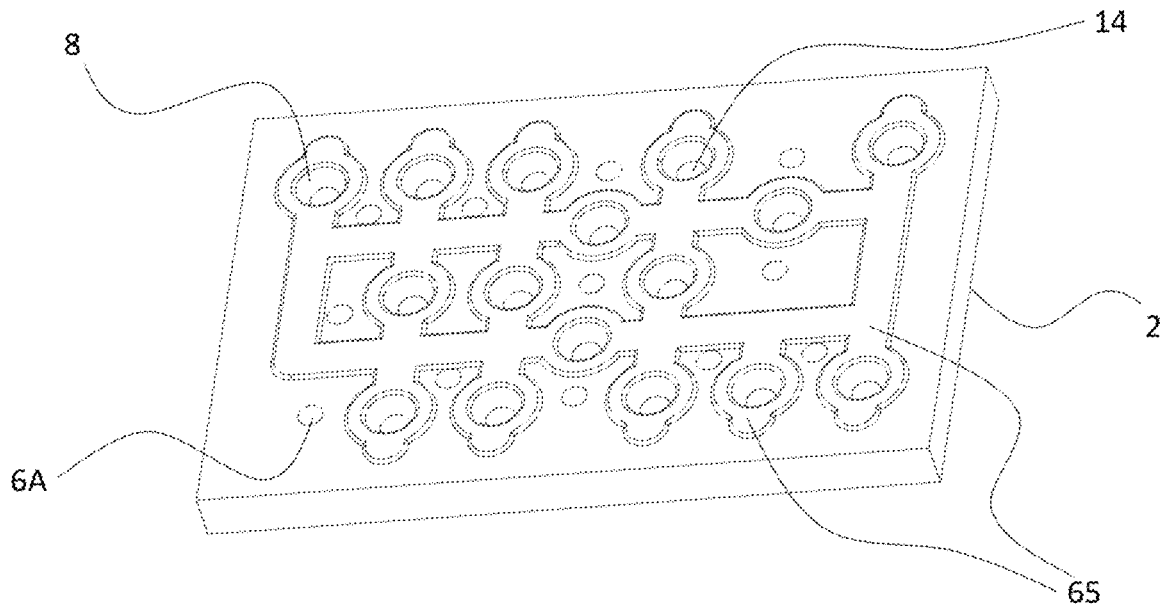
FIG. 11 is a perspective view of the inside surface of a cartridge's rear portion 2 including the sealing flanges 65 used for compressing and subsequently sealing the membrane (not shown).
Figure 13A:
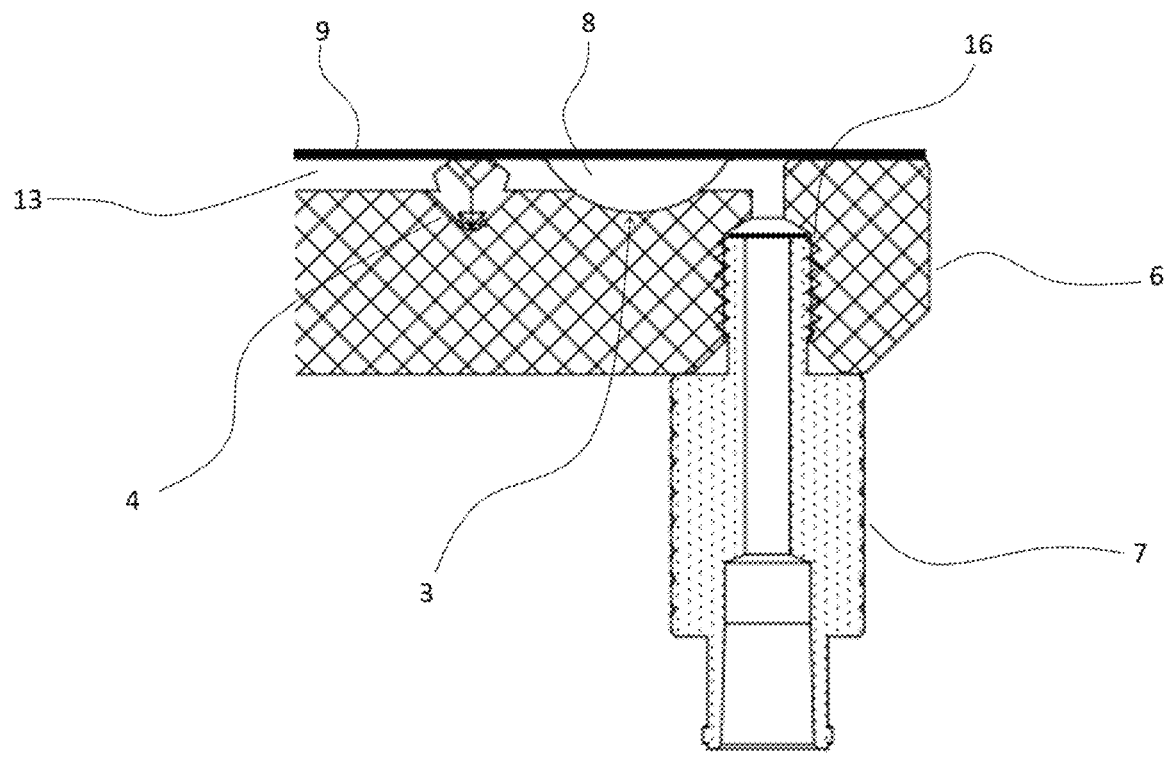
FIG. 13A is a cross-sectional view of a fluidic port 16 in the front side 6 of the cartridge as shown in FIGS. 10A and 10B, with a fluidic connector 7 inserted.
Figure 13B:
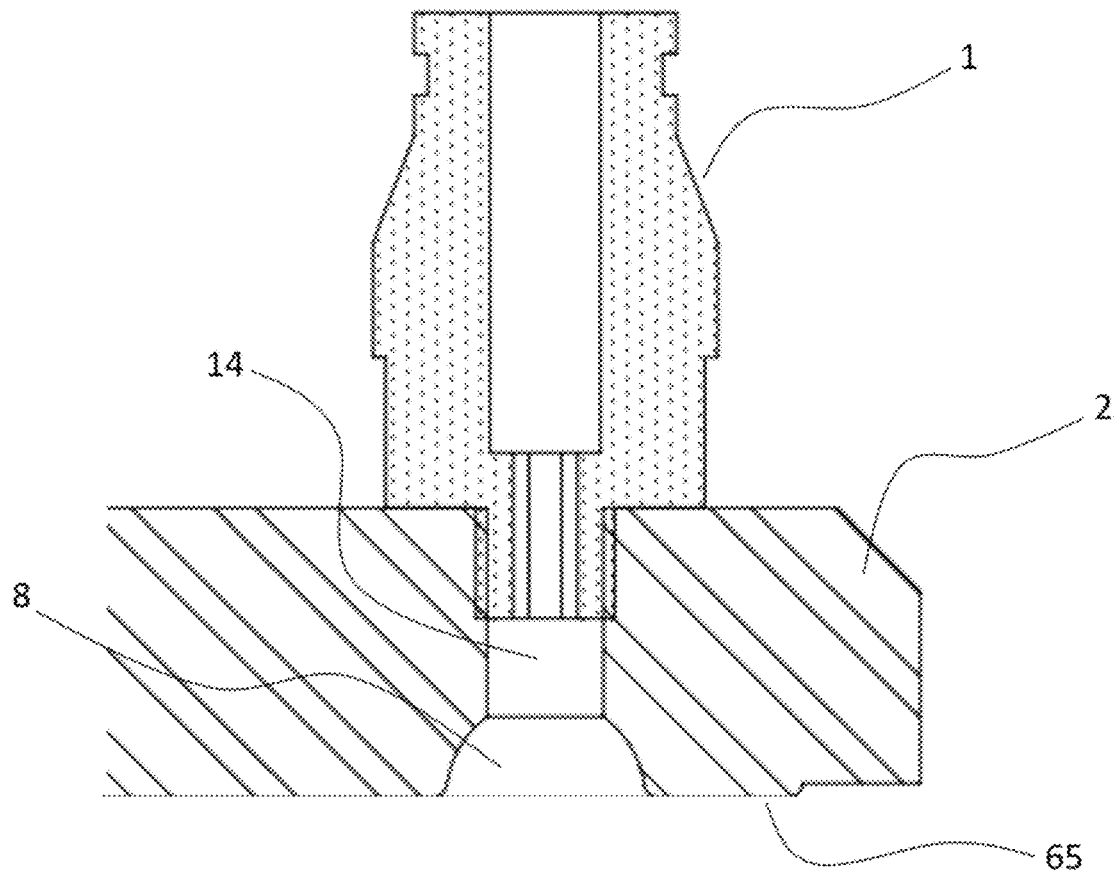
FIG. 13B is a cross-section of a pneumatic connector 1 screwed into a pneumatic port 14 in the rear side 2 of the cartridge 11.
Figure 14:
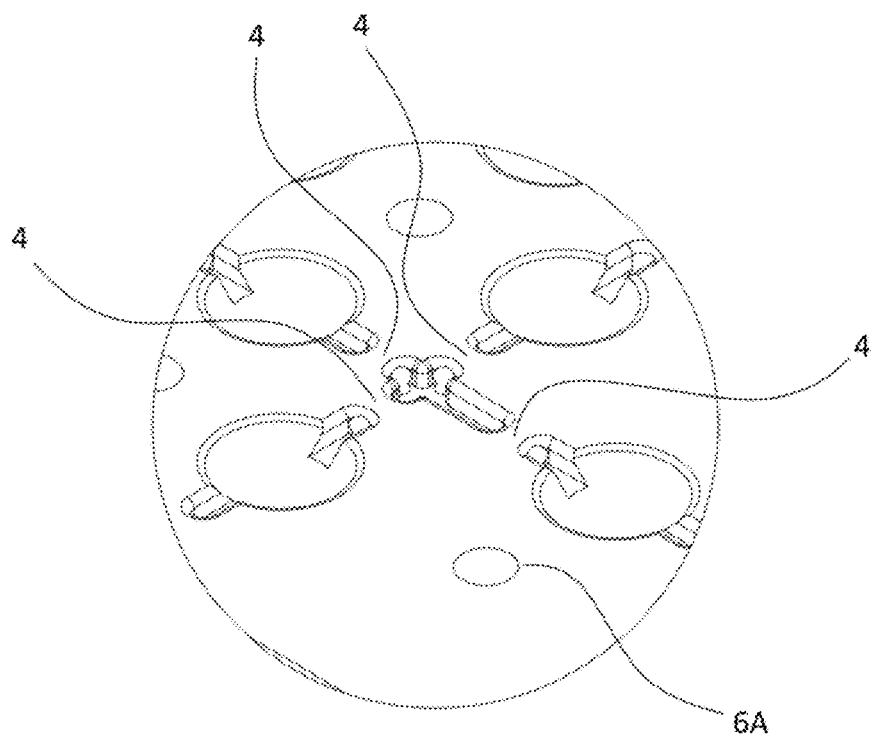
FIG. 14 is a plane view of a series of valves separated and sealed from each other (junctions between the valves are concealed).

FIG. 6 shows a close-up cross-section view of valve 3. The sealing around membrane 9 is enhanced by sealing flanges 65. The pressure port 14 supplies air via pneumatic connectors 1 to actuate the membrane 9 and close the valve 3. To avoid pressurized air leakage, the membrane 9 is compressed by flange 65 on the rear side 2, providing uniform compression to the area surrounding valve 3. See FIG. 11. Junction 4 routes the fluid under the surface of the front side and has an opening positioned for membrane 9 to cover and fully seal off channel 13, as best seen in FIG. 13A.

Applying compressed air to the pneumatic connectors 1 actuates the membrane 9 at each valve 3, as described above. Upon releasing the air pressure through the connectors 1, membrane 9 returns to its equilibrium position which opens valve 3 and allows the fluid to pass through and to channel 13.

Figure 7:
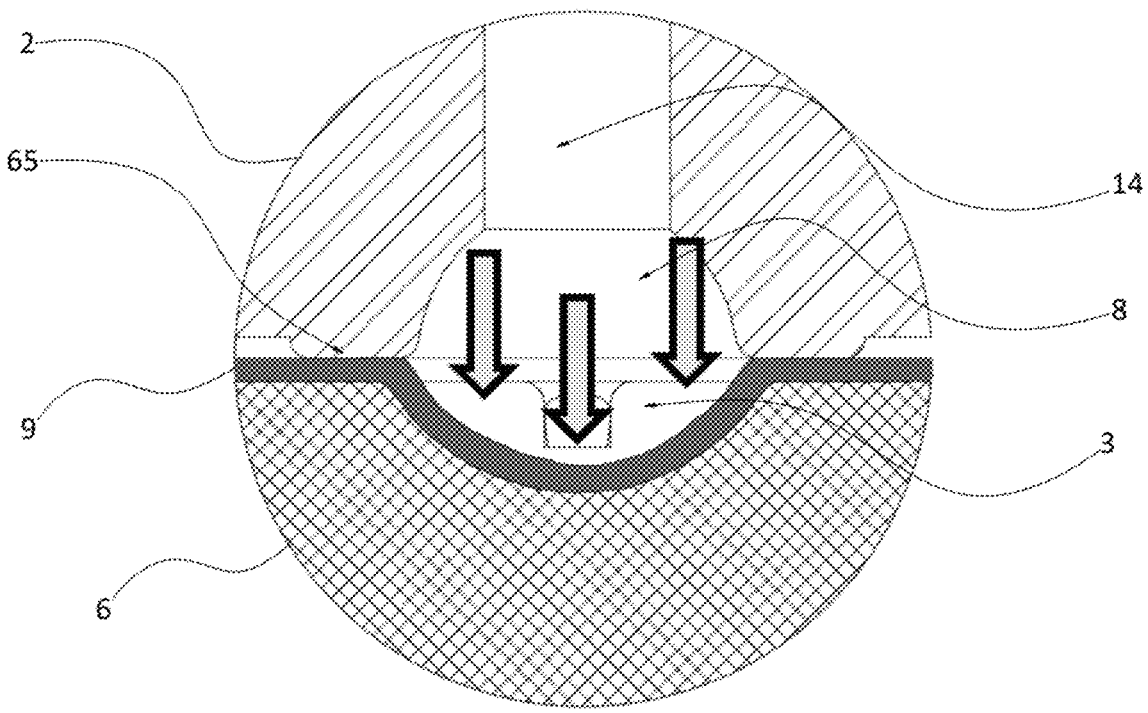
FIG. 7 is the same cross-section as in FIG. 6, but with the valve closed by air pressure applied through the port.
Figure 8:
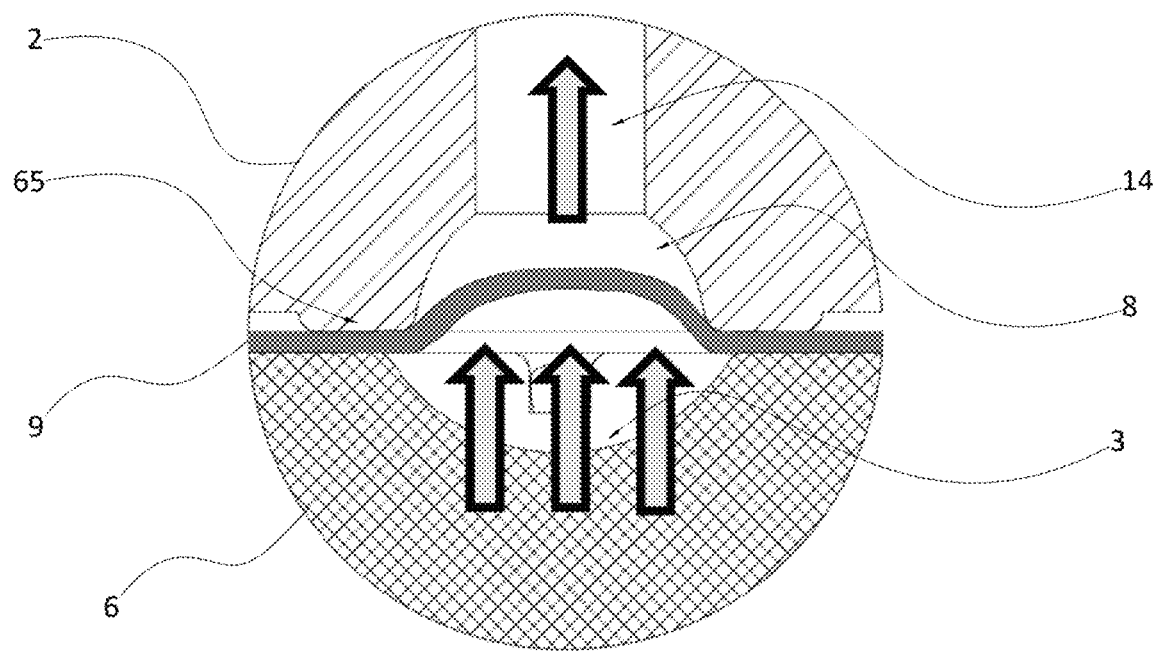
FIG. 8 is the same cross-section as in FIG. 6, with the valve opened and with a vacuum applied to the valve, whereby the membrane is prevented from moving to the closed position.

However, in some cases, especially when using a positive displacement pump for moving fluids, some valves could be subject to negative fluid pressures, which could cause the membrane 9 in unpressurized valves to slowly collapse. The collapse of membrane 9 would partially obstruct the flow, leading to an increase in negative pressure and further valve closure, eventually leading to full valve closure. To avoid this, one embodiment of the invention could use negative air pressure to open valve 3 and more quickly return it to its equilibrium state. This embodiment enables the fluid to be pumped at higher flow rates through channel 13, as negative liquid pressure will not cause a collapse of membrane 9 (thereby unintentionally closing valve 3). Furthermore, it allows valves 3 to be used to pump fluids, as when actuated in the right order with negative and positive pressure, they can move the fluid inside the cartridge by acting as a series of diaphragm pumps. An alternative embodiment of cartridge 11 could use pre-tensioning of membrane 9, which helps membrane 9 to resist low suction pressure from the fluid. FIG. 7 depicts valve 3 in its closed state, where pressure is applied to the pneumatic port 14. FIG. 8 depicts the valve 3 in its opened state with vacuum applied to the pneumatic port 14, pulling membrane 9 away from closed.

Cartridge 11 allows fluid to be routed between different fluidic connectors, using pneumatically-controlled valves 3, and eliminates the need for large pinch valves or solenoid valves. It also greatly reduces the amount of single-use tubing needed to create the array of fluid connections between all possible fluid networks—as needed to support adherent cell culture processes.

Figure 10A:
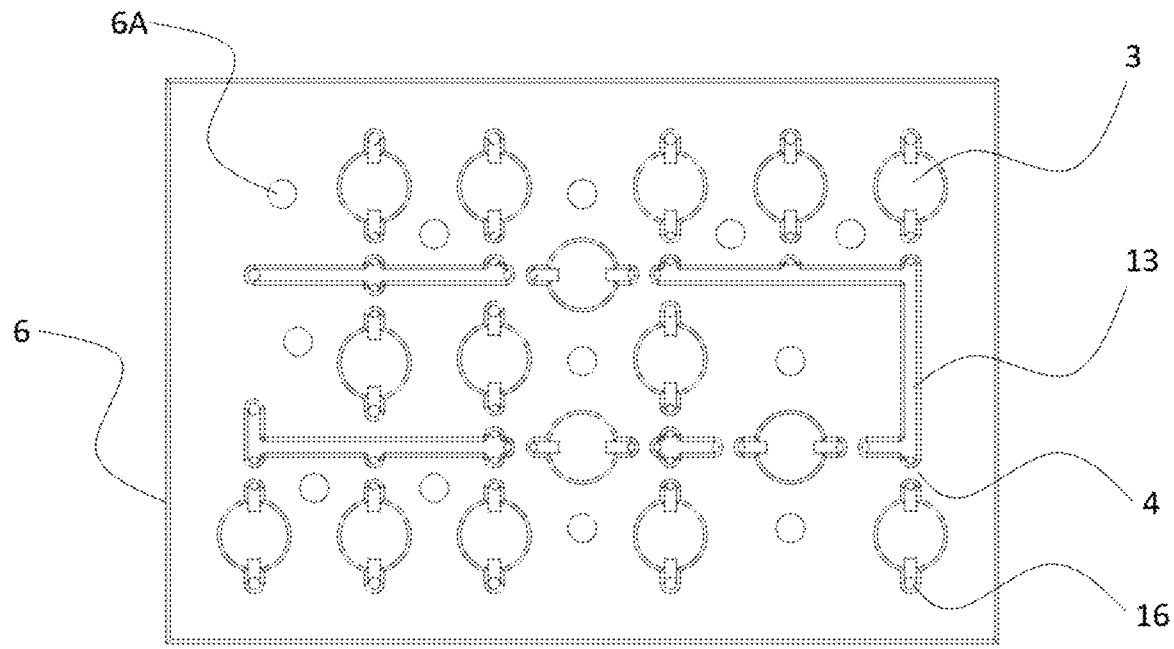
FIG. 10A is a plan view of a front portion 6 of a cartridge 11 showing valves, fluidic ports 16, channels 13, junctions 4, and holes for clamping screws 6A.
Figure 10B:
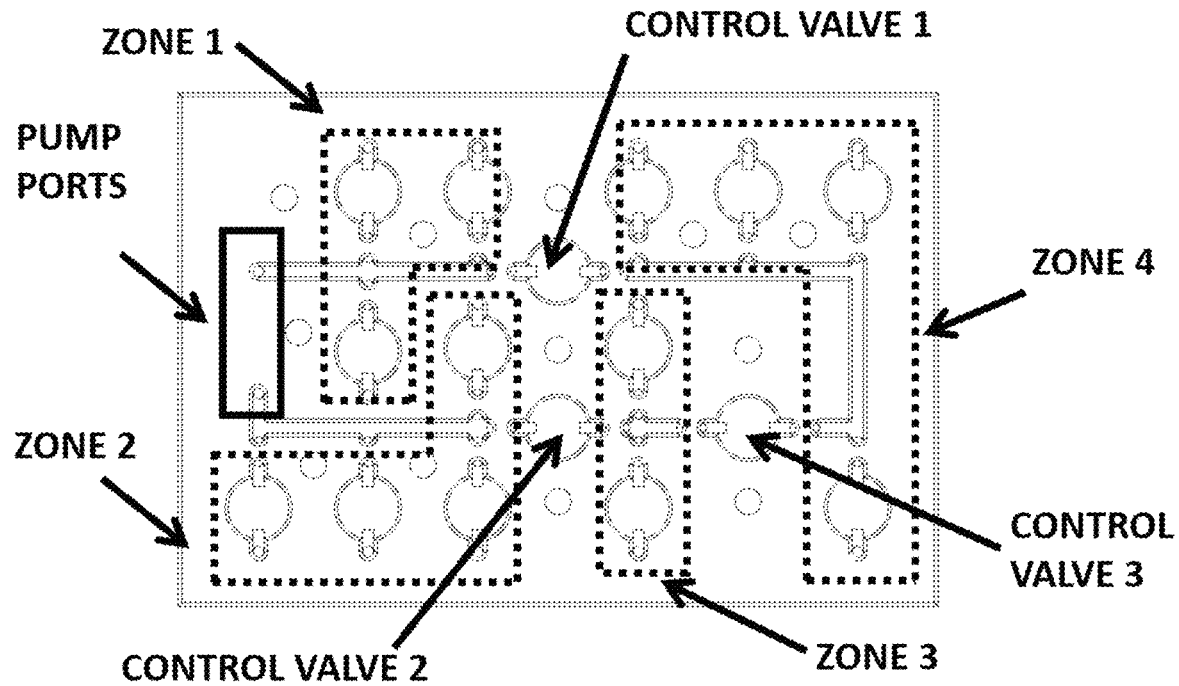
FIG. 10B is a plan view, of a front portion 6 of a cartridge 11 split into 4 different pumping zones between which the fluids can be moved with the use of control valves when a pump for fluids is connected to the pump ports in the cartridge.

As depicted in FIGS. 10A and 10B, the rear portion 2 of cartridge 11 is made of valves 3, fluidic ports (without connector 7) labelled 16, channels 13 and junctions 4. It also has a set of clearance holes 6A for clamping membrane 11. FIG. 10B shows a cartridge 11 split into several zones. Each zone has several fluidic ports between which the fluid can be moved via an external pump connected to pump ports. Pump ports are made in the same way as other fluidic ports.

One can move fluid in the system in FIG. 10B by connecting an external positive displacement pump to fluid connectors 7 (not shown) which are connected to the pump ports. The positive displacement pump uses tubing to transfer fluid in a sterile and safe way to and from the cartridge. This method allows the circulation of fluid from one zone in the cartridge to another by opening specific control valves. For example, to move fluid from zone 2 to zone 3, fluid would be pulled from one of the fluidic ports in zone 2, move through zones 1 and 4, and end up travelling to one of the fluidic ports in zone 3. Such an operation would require opening a control valve between zones 1 and 4, a control valve between zones 3 and 4, a valve from which the fluid is drawn in zone 2 and a valve into which the fluid is transferred in zone 3.

In one embodiment, a plurality of cell culture vessels are connected to a plurality of fluid connectors 7, all being within the same zone of the cartridge. Fluids can be transferred to, or from, the cell culture vessels by connecting the reagents to fluid connectors 7 which are in a different zone to the fluid connectors of the cell culture vessels. Fluids cannot be directly transferred between vessels located in the same zone, but require an intermediate step. Fluids can be transferred from one cell culture vessel to an intermediate receptacle located within a different zone to the one that the cell culture vessels are located. The fluid can then be transferred from the intermediate receptacle to a second cell culture vessel, which is located within the same zone as the first cell culture vessel. The intermediate receptacle may be a storage container, or a mixing chamber.

Figure 12:
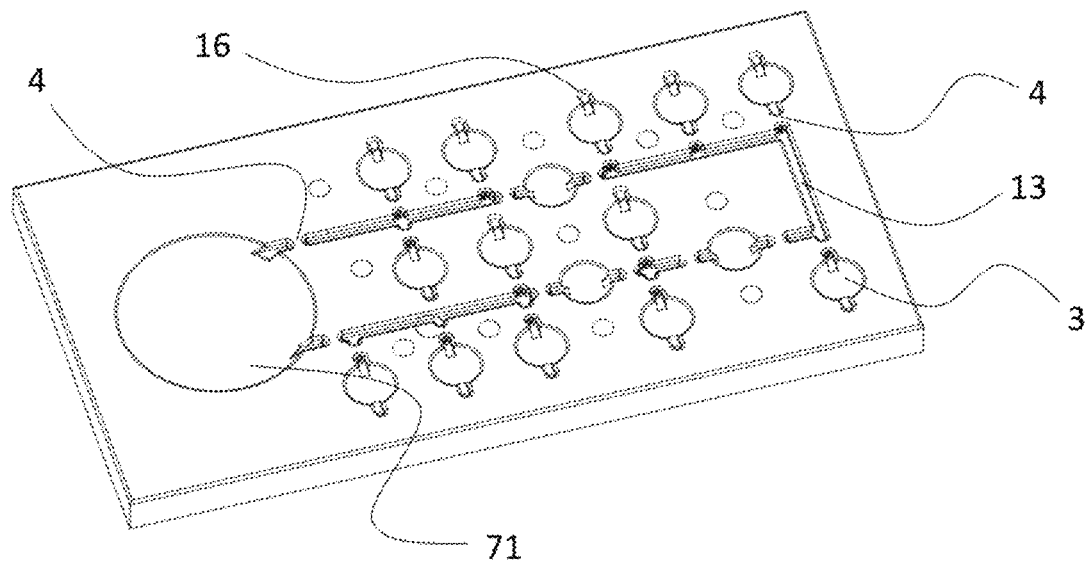
FIG. 12 is a view of a cartridge side with a diaphragm pump 71 at one end.

Another embodiment of the fluid distribution system could have a built-in pump which does not require any external connection between the cartridge 11 and the fluidic tubing. Such a pump could be but is not limited to the pressure-driven diaphragm pump 71 in FIG. 12, but could also include any other type of pump. Additionally, the number of zones in cartridge 11 is not limited to only four as shown in FIG. 10B, and can consist of more or less than four zones.

Fluids entering cartridge 11 include cell culture reagents such as growth medium, enzymatic dissociation reagents, cell suspensions, phosphate-buffered saline, water, ethanol, or other cleaning agents. Fluids exiting would pass to cell culture chambers, mixing chambers, heating chambers, and product receptacles. Due to the nature of the system, it must therefore be sterilized before being used for cell culture application.

Figure 4A:
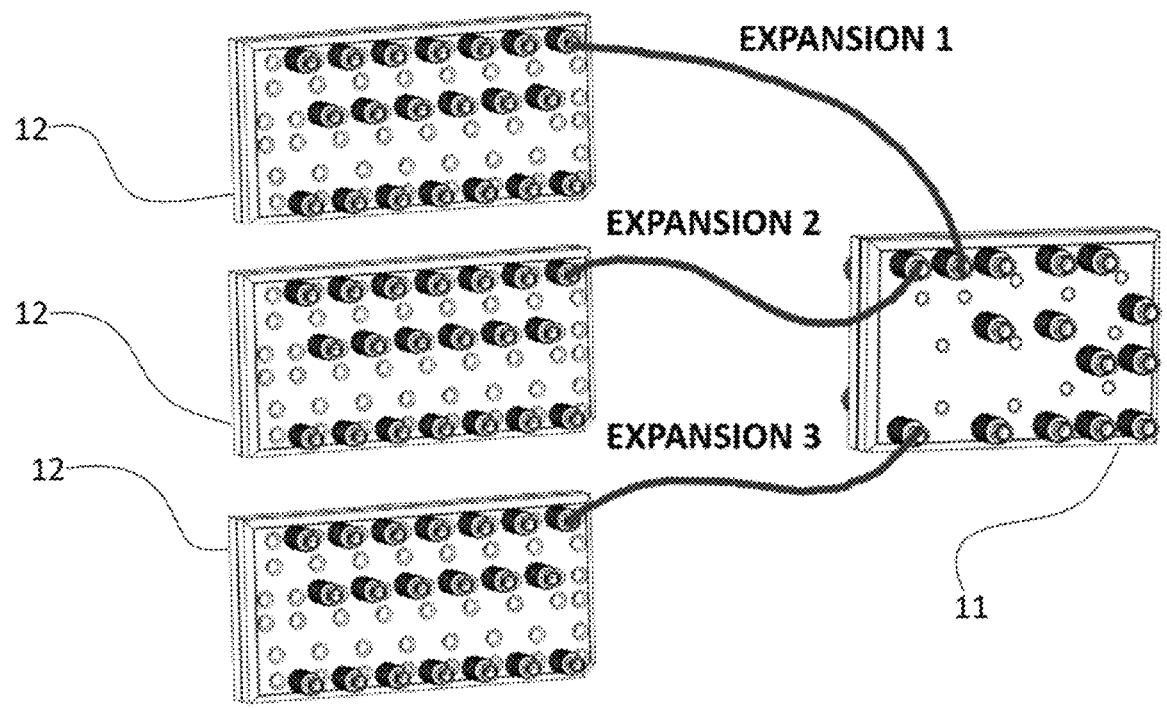
FIG. 4A is an elevational view of a main cartridge of FIG. 1 (rightmost) connected with similar expansion cartridges to enable multiple cartridges to be used. The expansion cartridges are connected directly to the main cartridge as stand-alone units.
Figure 4B:
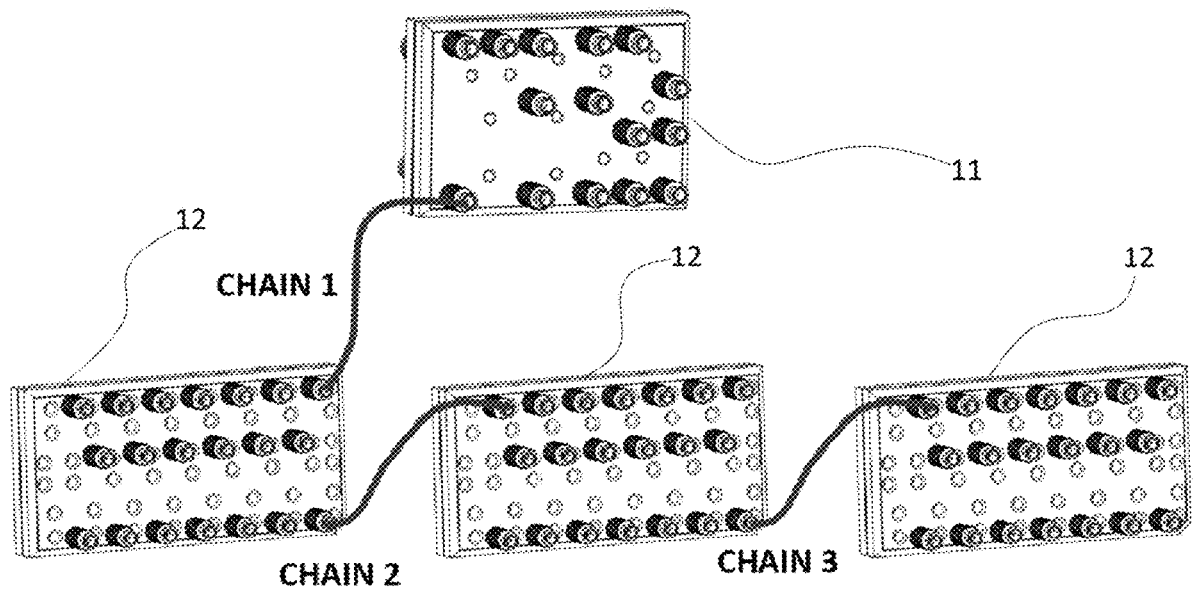
FIG. 4B is similar to the view in FIG. 4A, but the expansion cartridges are connected in a chain, and only one is connected with the main cartridge (topmost).
Figure 5:
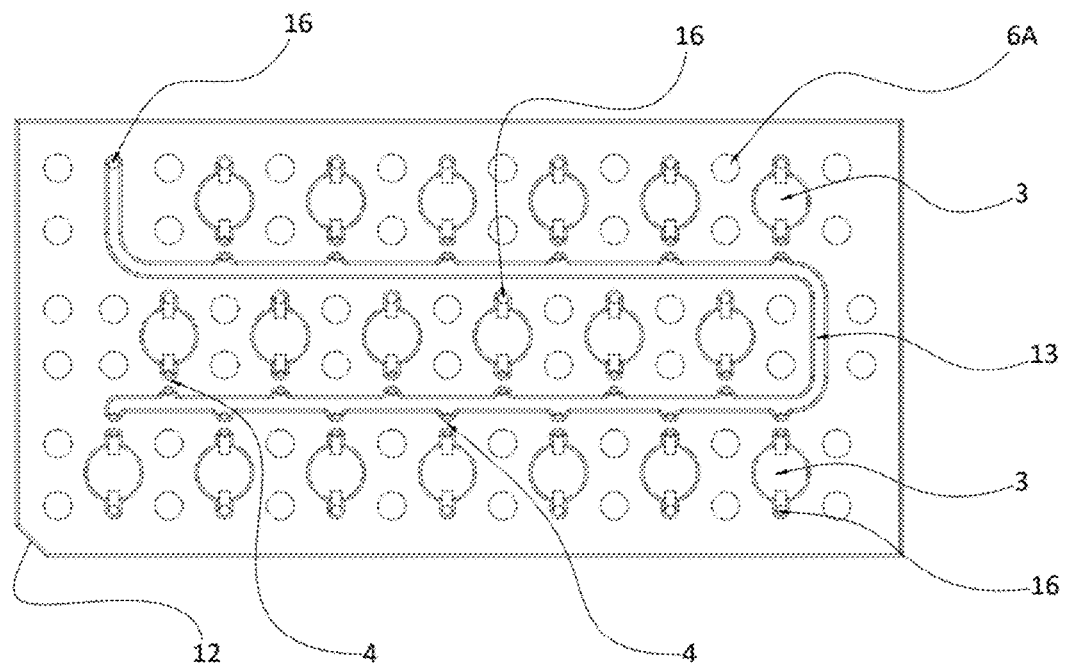
FIG. 5 is a plan view, partially transparent, of an expansion cartridge of FIGS. 4A and 4B, showing the fluid paths within the expansion cartridge, with no membrane and rear side in place and wherein fluidic ports attach to the main fluid path shown.

However, it is also possible to transfer different reagents or fluids into or out of the system depending on the end-user needs. As the cartridge 11 has a limited number of fluidic ports 16 this could lead to potential problems and reduce the invention's flexibility in wider cell culture applications. In such cases, one could use an expansion cartridge 12 with a larger number of fluidic ports 16 (See FIG. 5). The main difference between the expansion cartridge 12 and the cartridge 11 in FIG. 10B, is the number of zones in the expansion cartridge. The expansion cartridge 12 has only one zone and no control valves, while cartridge 11 in FIG. 10B has at least three zones and two control valves. One expansion cartridge 12, can only expand a number of fluidic ports in one zone of cartridge 11. Therefore, the invention could consist of several cartridges linked together, as depicted in FIGS. 4A and 4B. This solution would give the end-user greater flexibility in terms of inputs and outputs that are connected to the system at any point.

The cartridges 11 and 12 and its components are preferably made of biocompatible non-toxic materials such as PFTE, polystyrene, acrylic, polypropylene, nylon, polycarbonate, or bio-resin. The exception from this are the rear side 2 of cartridge 11 and any pneumatic components such as connectors or tubing that can be made of any suitable material.

Figure 9:
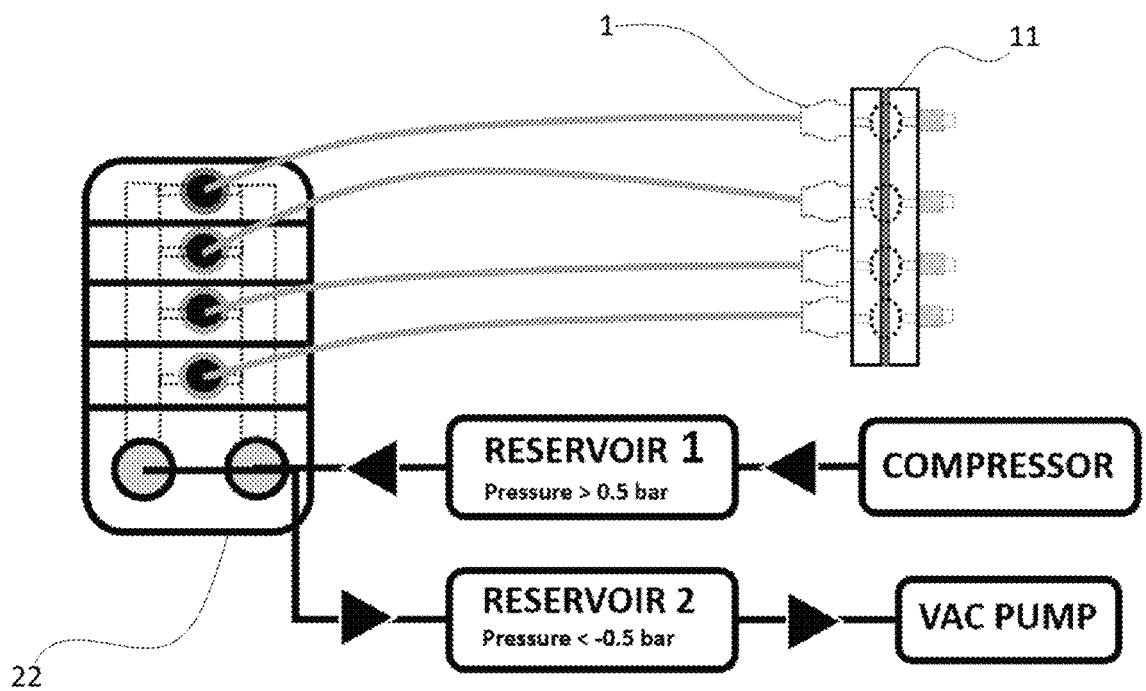
FIG. 9 is a schematic depicting switching between vacuum and air pressure applied to the valve ports.

Pressure control unit 22 in FIG. 9 helps in distributing the pressure and vacuum to multiple valves simultaneously. Pressure control units consist of multiple miniature solenoid valves that independently supply pressurized air or vacuum to each valve. By actuating these solenoid valves, one can therefore switch between pressurized air and vacuum for each valve in a cartridge 11. All valves 3 are connected to such control stations 22 for pressure distribution (other arrangements can also be used) as detailed in FIG. 9.

Figure 15A:
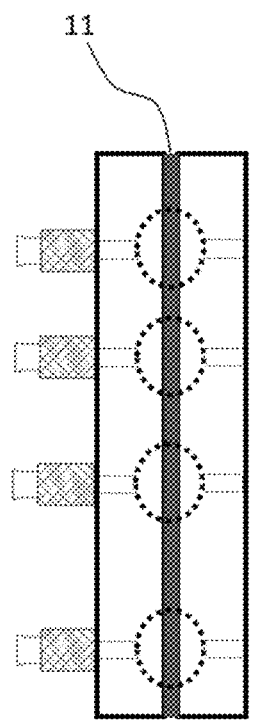
FIG. 15A depicts an elevational side view of a cartridge unconnected to the docking station, with valves partially shown.
Figure 15B:
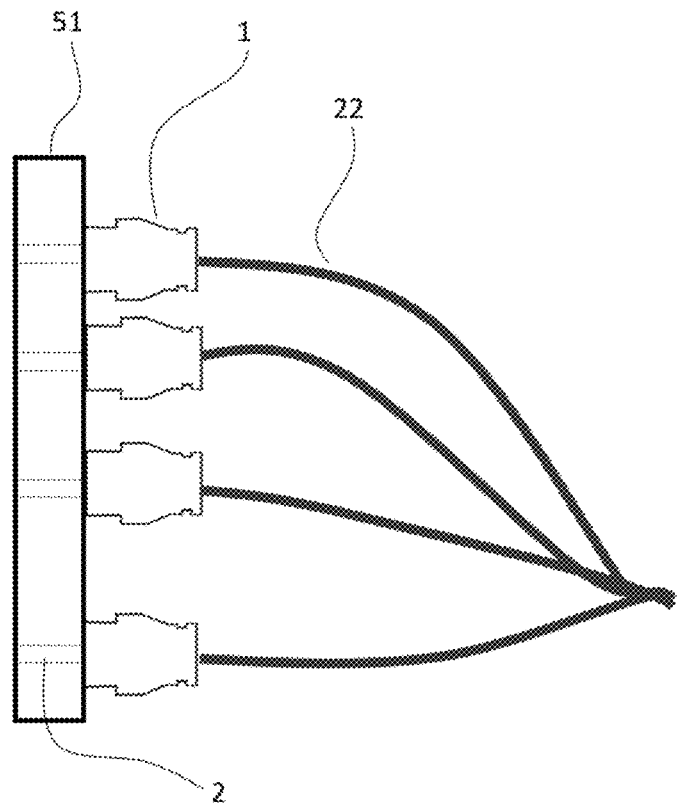
FIG. 15B depicts an elevational side view of a docking station for the cartridge in FIG. 15A.
Figure 16:
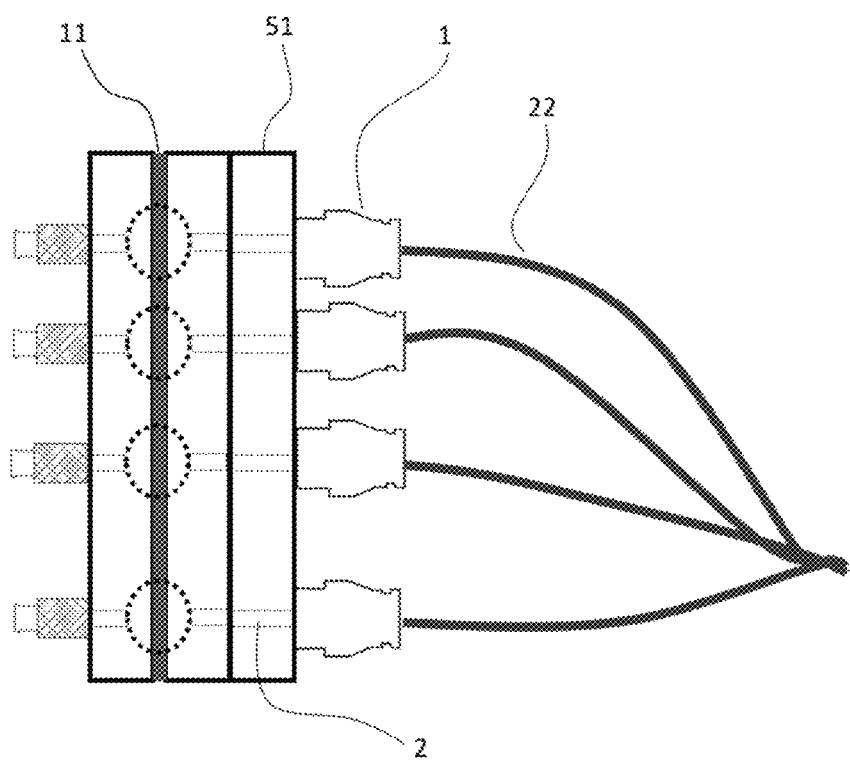
FIG. 16 depicts the cartridge of FIG. 15A mated with the docking station of FIG. 15B. The pneumatic lines are fluidly connected through the docking station plate to the cartridge.

The existing system has multiple air pressure ports 14 affixed with connectors 1 in the cartridge, which requires the user to re-connect all the connectors 1 to the cartridge 11 each time the cartridge is changed. If lines and connectors are connected improperly e.g. where lines are swapped, the system could fail catastrophically leading to a loss of expensive bioproducts. To avoid this problem a docking plate/station can be utilised as depicted in FIGS. 15A and 15B, which depict cartridge 11 and docking station 51 unconnected, while FIG. 16 depicts cartridge 11 connected to docking station 51. The resulting connection is between the pneumatic ports in the docking station and the cartridge. This method of docking removes the need to change pneumatic lines each time the cartridge is replaced.

Figure 23:
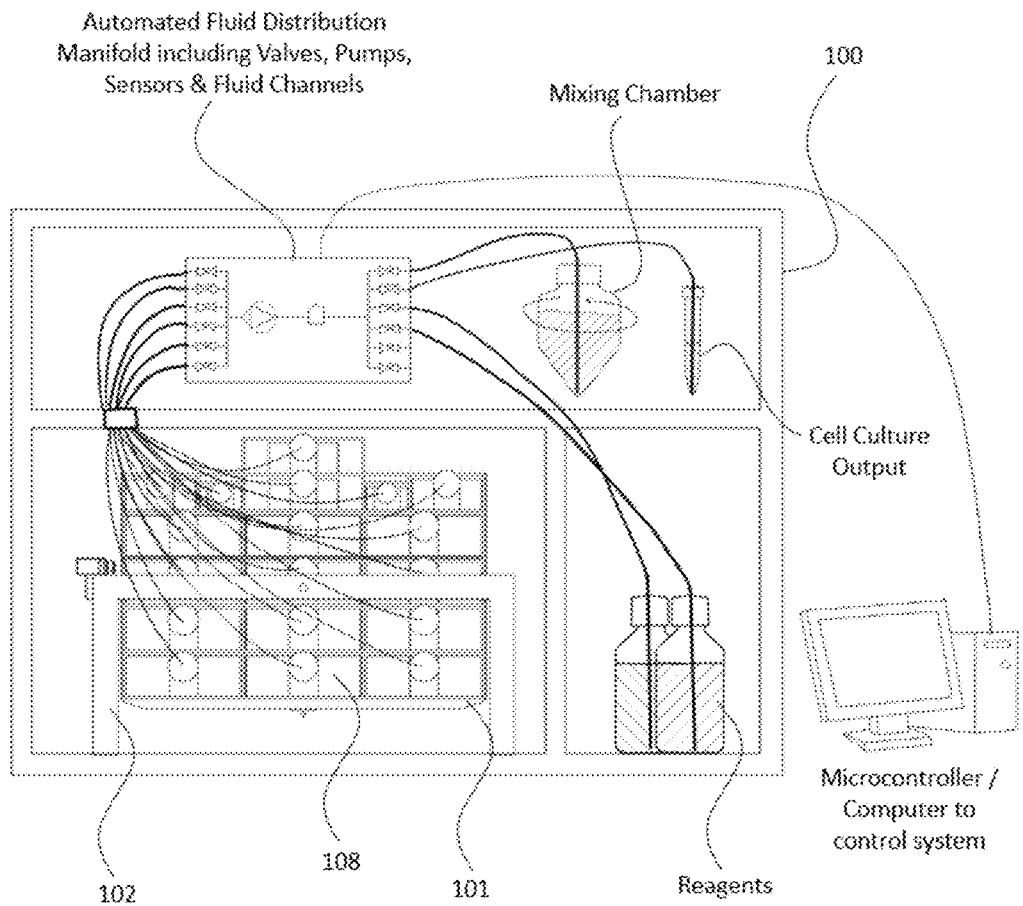
FIG. 23 is a schematic depiction of an automated cell culture system including a multi-axis rocker system.

As depicted in FIG. 23, showing automated system 100, the operation of the cartridge as described above can be controlled in an automated manner by connecting the pressure control unit and pumps to a computer or microcontroller which sends electrical signals to the valves and pumps in order to perform fluid routing and pumping steps without user interaction. Furthermore, the cartridge 11 can be used to move fluids into and out of the cell culture vessels mounted in chambers in the multi-axis rocking system shown in FIGS. 17 to 22B.

In another embodiment, the cartridge system could be used to route fluid to, or from, a mixing chamber which functions to mix reagents, and keep cells suspended homogeneously within reagents. The mixing chamber may be of various different designs, but fundamentally it agitates fluids via rotation, linear motion, vibration, pumping, or other means. The mixing chamber may also include functionality to warm fluids via heat pads, in-line heating, friction, peltier modules, or other means. As depicted in FIG. 23, the mixing chamber may be part of automated system 100.

Multi-Axis Rocking

Figure 17:
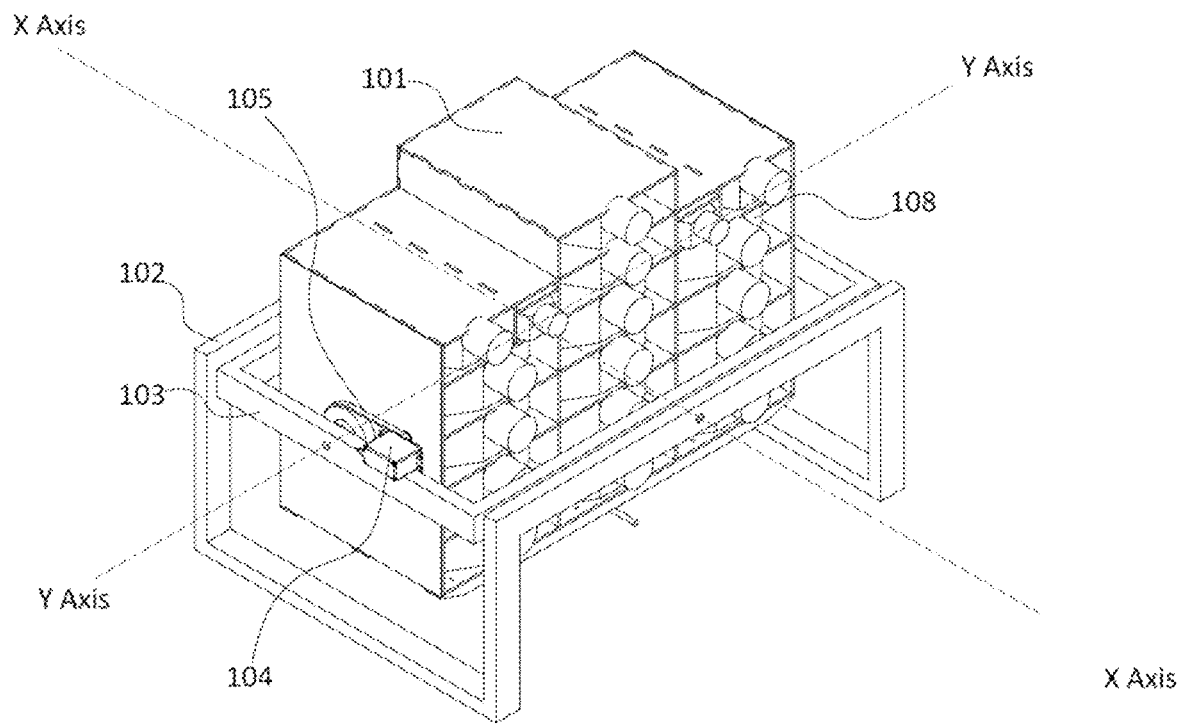
FIG. 17 is a perspective view of an embodiment of a multi-axis rocker system with oscillation about two transverse axes.
Figure 18:
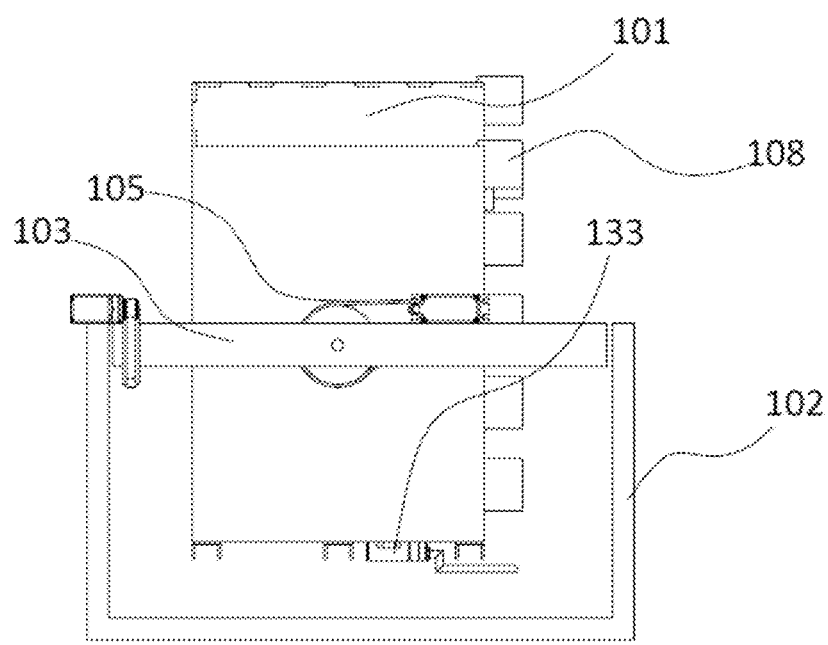
FIG. 18 is a side elevational view of the multi-axis rocker system of FIG. 17 depicting a level sensor 133 at the base.
Figure 19:
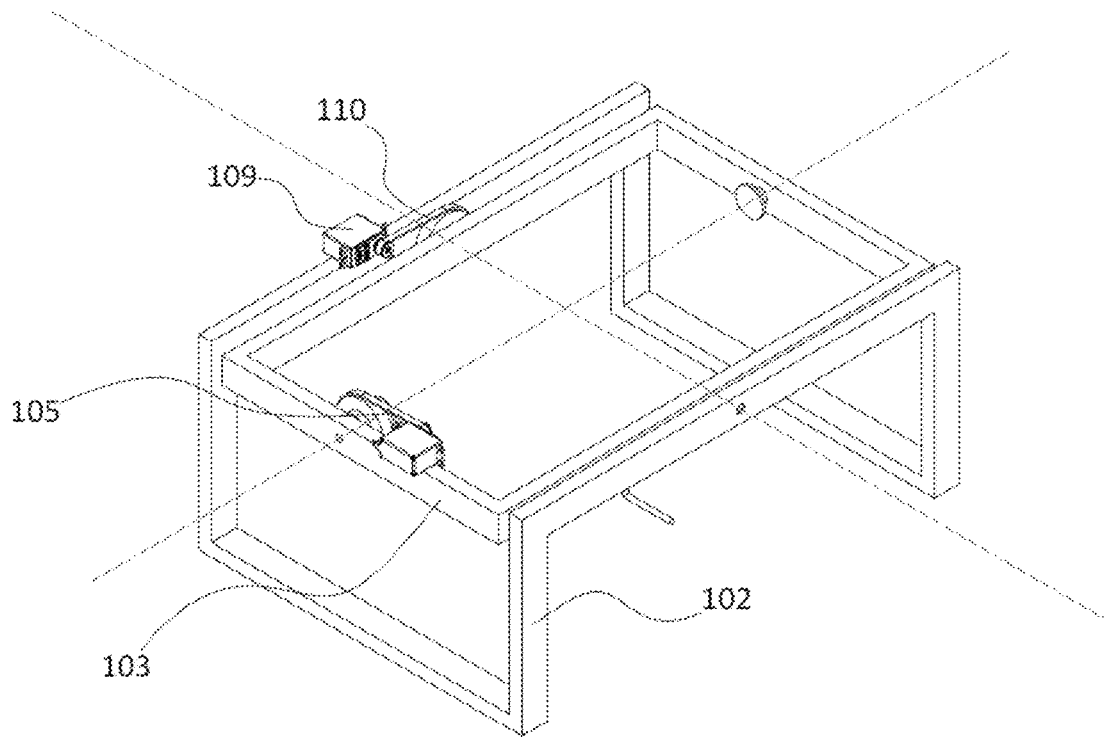
FIG. 19 is a perspective view of the frame of the multi-axis rocker system of FIG. 17 with the housing for the growth vessels removed and the X axis oscillation system visible.

This invention also integrates a housing 101 that allows control of cell culture vessel inclination in two or more axes. This is achieved via two, or more, nested frames 102, 103 which allow two, or more, orthogonal axes to be controlled independently, as depicted in FIG. 17. Cell culture vessels 108 are positioned within housing 101.

Each axis is controlled mechanically in a manner that preferably permits rotation of at least about 20 degrees either side of the neutral position. In one embodiment, the axes are controlled via a belt and pulley system, which is part of actuators 105 and 110, which is driven by electric motors 104 and 109, as depicted in FIGS. 17 to 20B. This system may incorporate gearing to create a mechanical advantage, and therefore reduce the required torque of the motor. One embodiment has a 5:1 gear ratio. The motors used to drive the pulleys may include, but are not limited to, servo motors, stepper motors, and DC motors. Other embodiments may be driven by other mechanical means such as gears, chain drives, or lead screws.

Figure 20A:
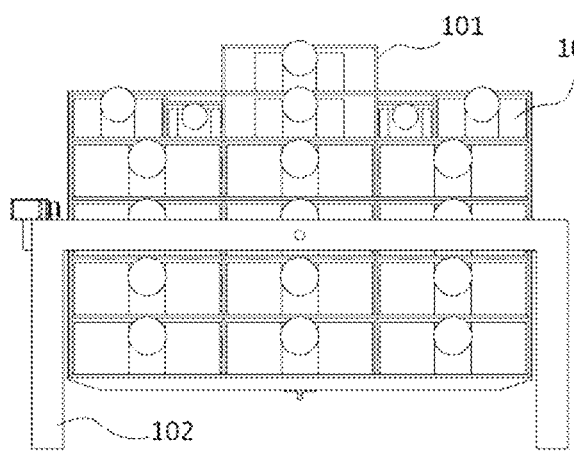
FIG. 20A is a frontal elevational view of the multi-axis rocker system of FIG. 17.
Figure 20B:
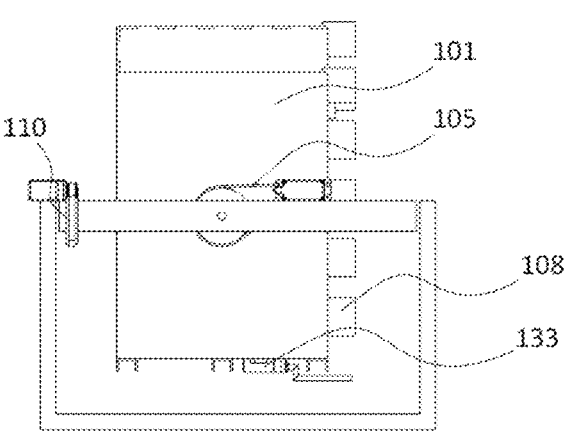
FIG. 20B is a side elevational view of the multi-axis rocker system of FIG. 17.
Figure 22A:
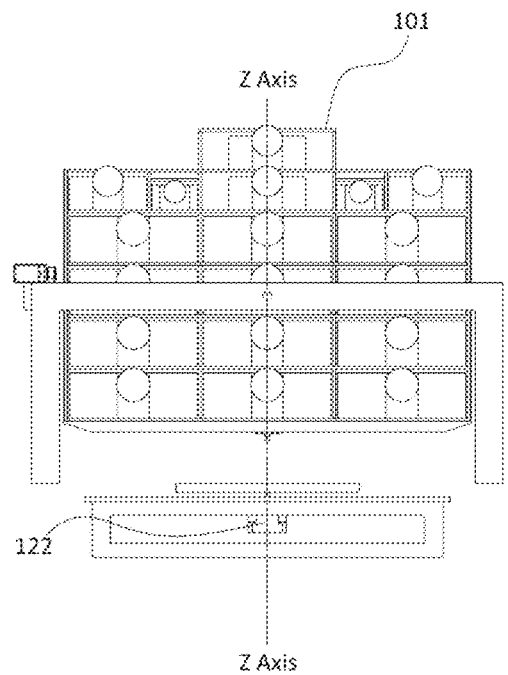
FIG. 22A is a frontal elevational view of the embodiment of the multi-axis rocker system shown in FIG. 21.
Figure 22B:
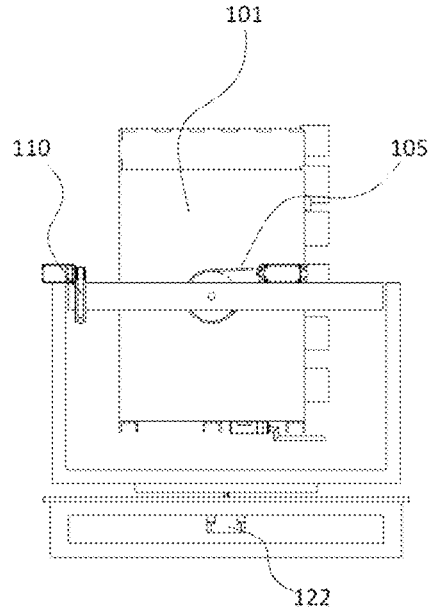
FIG. 22B is a side elevational view of the embodiment of the multi-axis rocker system shown in FIG. 21.

In one embodiment, cell culture vessels 108 are arranged within housing 101 to all lie in the same orientation, as depicted in FIGS. 20A and 20B. Preferably, the housing 101 allows the vessels to be inserted and removed through an open frontal port. In other embodiments, the port is fitted with a door which preferably can be locked to prevent vessels falling out. In other embodiments, unwanted movement of the vessels within the housing 101 is prevented by including hook and loop mating fasteners on the vessels and fixed inside the housing 101, or using high friction inserts fixed in the housing 101 which contact the vessels and prevent sliding. One could also use mechanical locking features such as sprung loaded plungers, latches, or straps.

In one embodiment, housing 101 is manufactured from a combination of sheet metal and plastic which is permanently joined together at joints via adhesive, welding, and/or interference joints such as finger joints. Plastic materials include polymethyl methacrylate (PMMA), polycarbonate (PC), polypropylene (PP), and high impact polystyrene (HIPS). Sheet metal materials include stainless steel, and aluminum.

In one embodiment, the frame structure for the nested multi-axis rocker is manufactured from metal like aluminum, which may be welded or assembled using fixtures such as screws, bolts, rivets. Plain bearings, ball bearings, or roller bearings are used to reduce friction where axles have relative motion to other components that they pass through.

Precise positional control of the culture vessel tilt is achieved by coupling the actuators 105, 110 with inclination sensors, or accelerometers. Sensors 133 may be mounted to the flask housing (see FIG. 20B), or directly to the culture vessels, to allow measurement of the tilt in two, or more, axes. Inclination sensors preferably have high accuracy, allowing control of the level of the culture vessels in two or more axes to ±0.1°, or better. Sensors 133 provide positional feedback to the actuators 105, 110, which can then adjust the tilt of the culture vessels until the desired position is achieved within the acceptable tolerances. In another embodiment, multiple sensors are used which provide positional feedback on different parts of the system.

Figure 24:
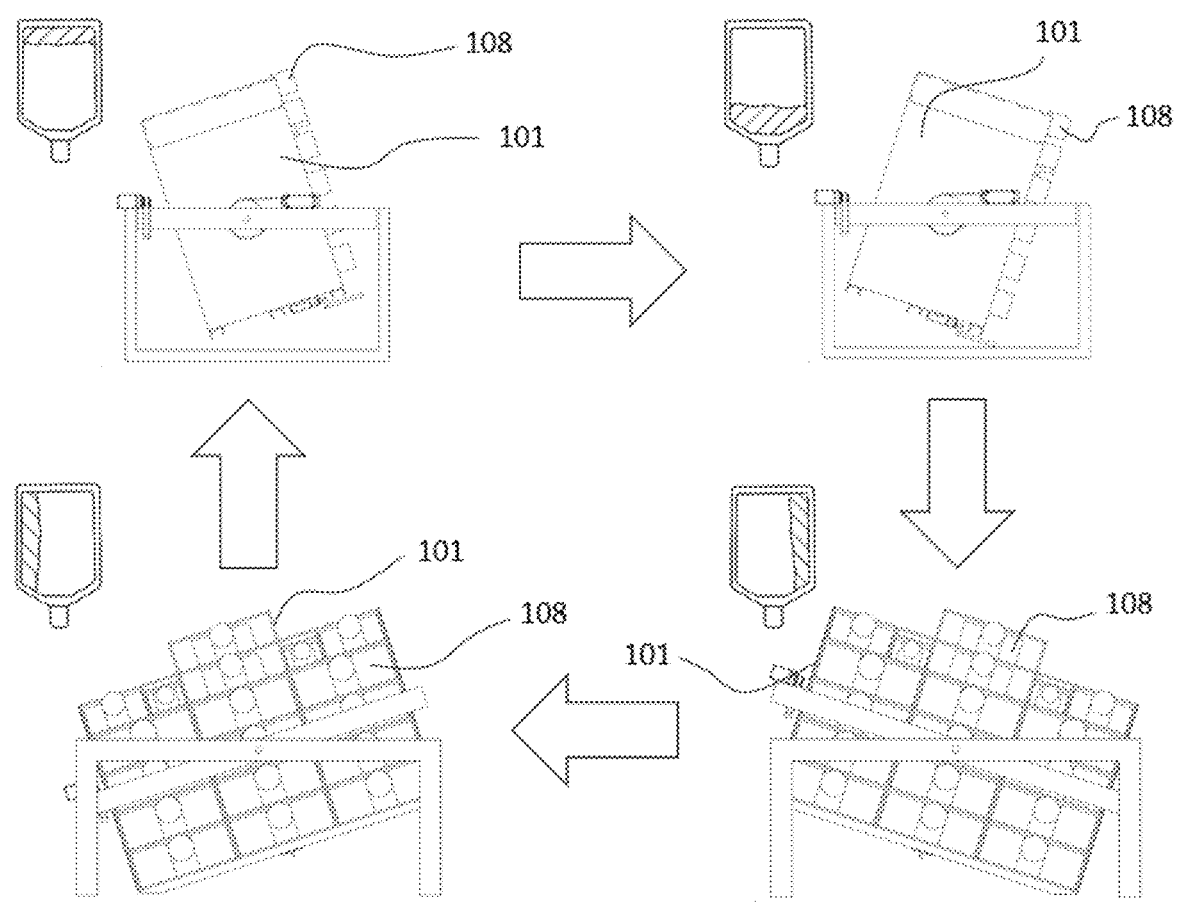
FIG. 24 schematically depicts possible fluid positions within vessels (though the vessels would be held in the substantially horizontal orientation, not vertical as shown) at various positions of the multi-axis rocker system.
Figure 25:
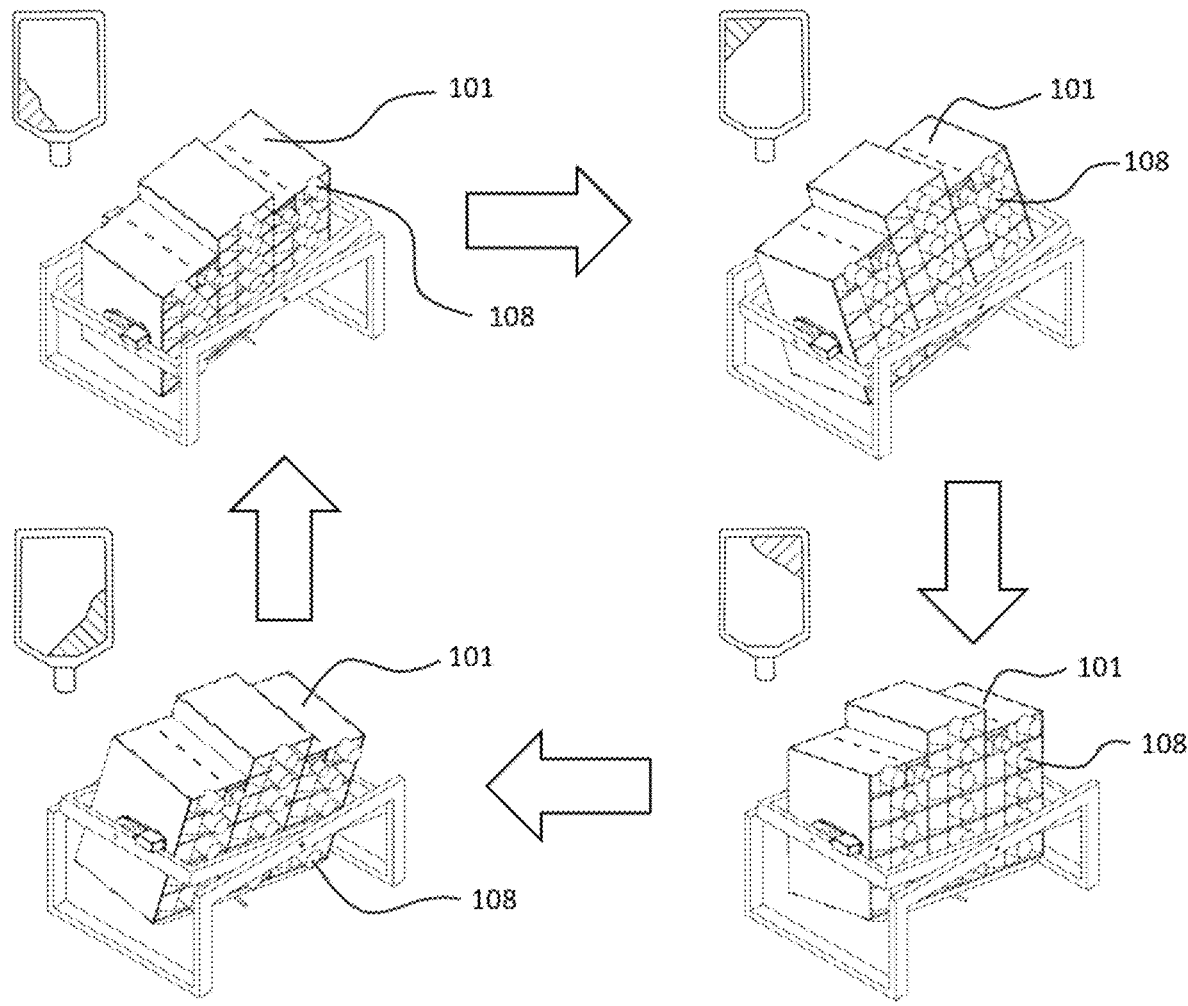
FIG. 25 schematically depicts possible fluid positions within vessels held in the substantially horizontal orientation, when rocker system positions are shifted to move the fluid around the inner circumference of the culture vessels in a swirling motion.

The system allows the fluid within the culture vessels to be positioned or moved as required to optimize cell culture steps. Such fluid motions include, but are not limited to, pooling fluid into desired positions (e.g. at the corners), rocking back and forth or side to side, swirling the fluid, random motion of the fluid, vibration, waves, and creating an accurately leveled fluid layer. Some fluid positions within a vessel 108 are shown in FIGS. 24 and 25, beside the position of the housing 101 where that position would occur. Vessels 108 are shown in vertical position but would in fact be oriented the same way as housing 101. These fluid motions also allow cell culture motions generally performed manually to be simulated by the system 100, hence facilitating automation of all steps.

Another embodiment integrates a rocking platform that allows control of the culture vessel inclination in 3 axes. The third axis is achieved by including a third gimbal 122 (FIGS. 21 and 22A, 22B) which allows the multi axis system to rotate about an additional vertical axis. The third gimbal 122 uses a motor to control movement and orientation.

A rocking motion of fluid within culture vessels can be generated by performing one, or more, cycles of a back-front rocking motion followed by one, or more, cycles of a side-side rocking motion as shown in FIG. 24. This motion helps to spread fluid to all parts of the culture vessels, and mix reagents. In one embodiment the angles of the culture vessels during the rocking process is as described in Table 1 Below:

TABLE 1 rocking motion tilt angles

| Motion | X Axis | Y Axis |
| --- | --- | --- |
| Backward | 0° | −15° |
| Forward | 0° | 15° |
| Right | 15° | 0° |
| Left | −15° | 0° |

Figure 26:
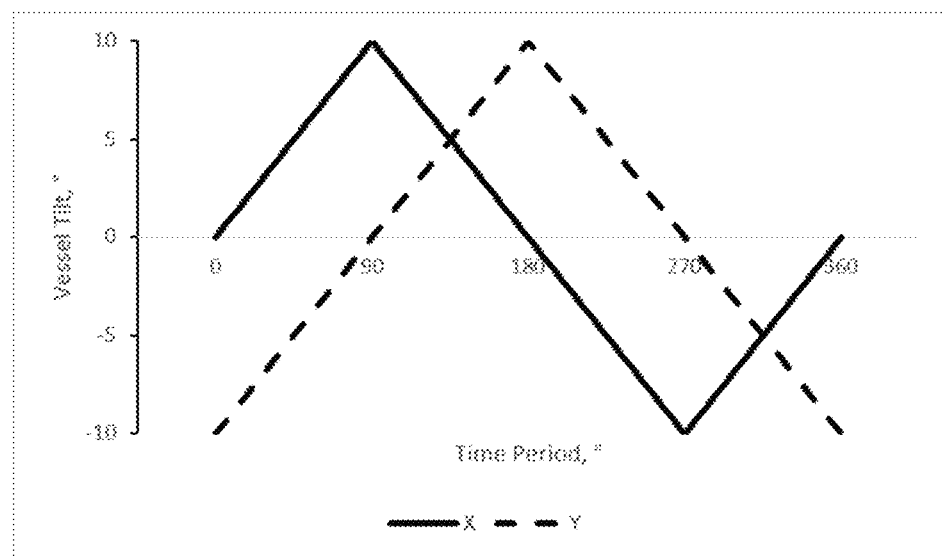
FIG. 26 is a graph of the angular motion on each axis during a single swirling cycle as shown in FIG. 25.

A swirling motion of the fluid within the vessels (within housing 101) can be generated by performing one or more cycles where the culture vessels move in an elliptical motion, thereby forcing fluid to move around the inner perimeter of the culture vessels in a continuous loop. This motion is depicted in FIG. 25. The inclination of each axis of the housing 101 and the culture vessels 108 during one swirling loop is depicted graphically in FIG. 26.

All motions possible in the two axis embodiments (FIGS. 17-19) are possible in the three axis embodiment (FIGS. 20A to 22B), but the additional axis adds the possibility of a side-side twisting motion about the vertical axis. This could be used during the dissociation and seeding stages of passaging. Additionally, it enables cell culture vessels and interfaces to be pointed in a certain direction about the vertical axis to allow subsystems and users to interact with the system from different sides.

Figure 27:
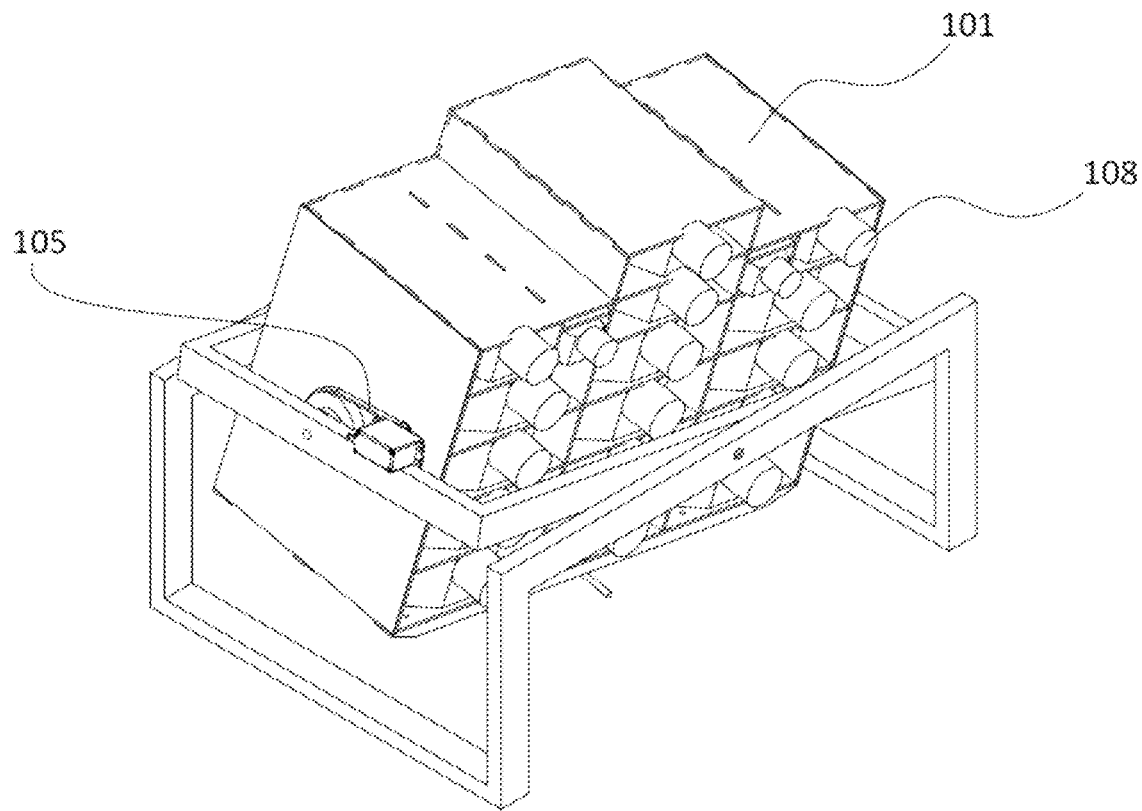
FIG. 27 is a perspective view of an embodiment of the multi-axis rocker system wherein the culture vessels are at a specified inclination in each of two axes.
Figure 28:
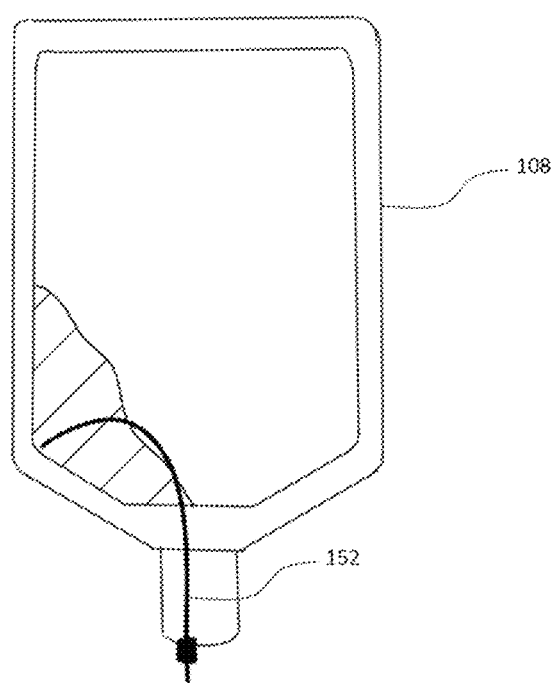
FIG. 28 depicts an embodiment of a vessel in the substantially horizontal position showing the fluid position in the vessel when the rocker is held at a particular angle in each two axes. The vessel is drawn in the vertical position to enable a view of the fluid within the vessel.

The control of tilt in two orthogonal axes (X and Y) allows fluid to be pooled around the inner perimeter of the culture vessels. This may be used to pool fluid in a corner of the culture vessels to allow fluid to be fully drained. FIG. 27 shows the multi-axis gimbal system being used to tilt the vessel in the culture vessels 108 to a specific angle to pool the fluid in a desired location, e.g., as shown in FIG. 28.

The system allows connection of tubing, and other fluid network components, to the cell culture vessels. This opens the possibility of automated control of fluids into and out of the vessels by using control systems and pumps including peristaltic pumps, diaphragm pumps, piston pumps and vane pumps. In addition, the system may also use pressure driven pumps.

Interfaces with the vessels allow connection of pipework directly to the vessels such that each vessel can be filled and drained individually. The interfaces are located such that fluid can be pooled around the interface, and therefore complete fluid withdrawal is possible. FIG. 28 shows semi-rigid bent tubing 152 routed into the corner of a cell culture vessel 108 (depicted as lying vertical, but which would actually lie substantially horizontal) which allows fluid to be drawn out from that corner. Other interfaces between the vessel and the fluid may include the use of needles or flexible tubing.

One embodiment of the device uses commercial cell culture vessels which are designed for adherent cell cultures. This type of culture vessel includes T-Flasks, Petri dishes, and square culture dishes. Additionally, multi-layer flasks such as the Nunc™ Cell Factory™ (ThermoFisher Scientific) could also be used wherein the multilayer flask is attached to the multi-axis gimbal system to rotate it, and proprietary interfaces are used for fluid interfaces. These commercial flasks may be manufactured from homopolymer or copolymer polycarbonate or polystyrene, or from glass. Surface treatments may be used on the growth vessel inner surfaces such as plasma treatment, or other treatments designed to promote cell adherence. Another embodiment includes coating the lower surface of the culture vessels with extracellular matrix proteins such as collagen or fibronectin. The surface coatings may be applied before the culture vessels are inserted into the system, or the coating may be applied as part of the cell culture protocol within the system.

Another embodiment uses customized adherent growth vessels instead of commercially available options. Custom cartridges may be able to reduce the footprint of the system, and allow it to be set up and used more easily by the user. Custom growth vessels may be individual vessels, or multiple vessels contained within one unit via stacking them in layers or arranging multiple vessels in the same layer. These may be manufactured from homopolymer or copolymer polycarbonate or polystyrene, or from glass. Surface treatments may be used on the growth vessels' inner surfaces, such as plasma treatment, or other treatments designed to promote cell adherence. Another embodiment includes coating the lower surface of the vessels with extracellular matrix proteins such as collagen or fibronectin. The surface coatings may be applied before the culture vessels are inserted into the system, or the coating may be applied as part of the cell culture protocol within the system.

One embodiment of the system uses adherent mammalian cell types such as pluripotent stem cells, embryonic or induced. Further this includes their differentiated progeny such as but not limited to, retinal pigment epithelial cells, skeletal muscle cells, adipocytes, cardiomyocytes and hepatocytes. Multipotent progenitor cells such as mesenchymal stromal stem cells, myosatellite stem cells, and neural stem cells. Further, this includes their differentiated progeny such as but not limited to, skeletal muscle cells, adipocytes, chondrocytes, osteoblasts and neurons. Mature somatic cells such as but not limited to, fibroblasts, keratinocytes and hepatocytes. Finally, commercially available cell lines such as Chinese hamster ovary cells or human embryonic kidney cells, that are commonly used in the production of various biologics. Any of these cell types may be from human, or animal origins.

Automating the Passage of Anchorage Dependent Cells

Adherent cell culture is difficult to automate due to the need to detach cells from their growth surfaces and re-seed them onto larger growth surfaces when they reach confluence, which may be needed every few days, depending on cell type. This process is called passaging. To maintain uniform and continuous growth, adherent cells need to grow or expand before they are confluent. Confluence is defined as the total mass of adherent cells taking up a certain percentage of the total available surface area for cells to adhere and grow to in a cell culture vessel. For example, a specific cell type might reach confluence at 80%—i.e. the dividing cells have taken up approximately 80% of the available surface area in a given cell culture vessel. Once the threshold for confluency has been reached, the cells need to be passaged or placed into larger vessels with more available surface area for cell adhesion and growth. If this is not done the cells can begin to experience retarded growth, cellular function and ultimately cellular death.

Passaging creates fluid handling challenges, and general scale-up challenges because the system needs to be capable of starting with very small growth surfaces (and fluid volumes), and splitting cells out several times onto final growth surfaces which may be 10-1000+ times larger than the surface area of the starting cell culture vessel.

Figure 31:
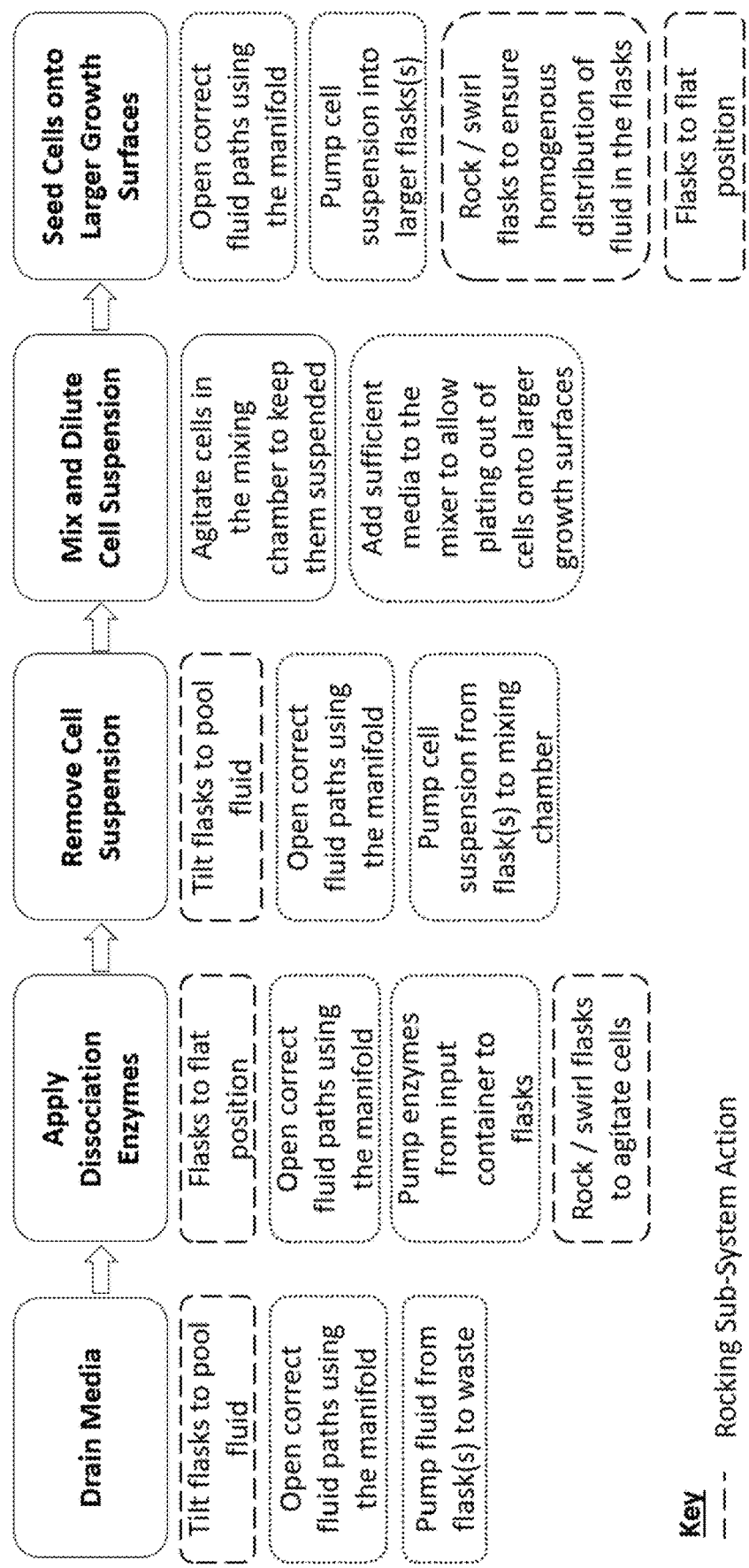
FIG. 31 is a flowchart showing the process steps required to passage and grow adherent cells within the automated system of the invention.

This invention combines a novel cartridge-based fluidic handling system and a novel multi-axis gimbal rocking system to automate the process of passaging anchorage-dependent cells in single, integrated device or instrument. A summary of the passaging process within the automated system is depicted in the flow chart in FIG. 31.

The invention industrialises the process of passaging adherent cell culture by replacing the manual steps involved in passaging (Dissociation, Splitting and Seeding-detailed below) with machine-driven steps for cell culture performed in commercially available T-flasks, or other standard cell culture vessels, or proprietary designed cell culture vessels. This system automates the process of passaging cells using enzymatic techniques. Growth vessels of various sizes are used within the system to allow cells to be passaged several times, at various split ratios. Some embodiments of the system could also use additional reagents during a cell culture process depending on end-product needs. An example would be the addition of antibiotics such as Penicillin or Streptomycin to media used during the passaging process to prevent bacterial infection.

Dissociation

This is the process of adding dissociation reagents into a confluent cell culture vessel, evenly distributing and ultimately removing said reagents to cleave the bonds anchoring adherent cells to the cell culture vessels. The final step of the dissociation process is the creation of a cell suspension—where single cells or colonies of cells depending on cell type—will be suspended in media and can be split into subsequent cell culture vessels. Dissociation is usually accomplished by hand using a pipette or serological pipette to add and remove dissociation reagents in a sterile, tissue culture hood.

The system achieves this step by performing the following actions:
1) The culture vessel is rotated in two axes to pool the fluid into the desired location for emptying, such as the corner of the vessel. This allows different reagents to be pumped in and out of the culture vessels.
2) The cell culture medium is removed from the confluent cell culture vessel and cells inside the vessel are washed gently with phosphate-buffered saline (PBS). The wash is conducted by adding PBS to the culture vessel and using a rocking system to thoroughly distribute PBS across the entire culture vessel area. PBS prevents cells from rupturing or experiencing osmotic pressure-related stress or cell death and removes remaining media from the culture vessel acting as a cleaning agent for cells.
3) The PBS wash is then removed from the flask, and pre-warmed enzymatic dissociation reagents (e.g. Accutase or TrypLE™ marketed by ThermoFisher Scientific) are delivered to the culture vessel to initiate the passaging.
4) When the dissociation reagent is moved to the culture vessels, the multi-axis gimbal initiates a rocking motion lasting multiple minutes. The multi-axis gimbal allows rocking and swirling motions of dissociation reagents within the cell culture vessels. This agitates the cells adhered to the bottom of the growth vessels by applying shear forces to them, thus helping them to detach during the passaging process. In another embodiment, the multi-axis gimbal could be used to provide vibrating motion to the growth vessels, further helping the cells in the vessels to detach.
5) The fluid control system adds in cell culture media which may or may not have any additional additives (e.g. antibiotics to prevent contamination) to create a cell suspension-defined as cells floating in a liquid solution.

Splitting

Once the cells from the confluent cell culture vessels have been dissociated and suspended, either in single cell, aggregates or colonies depending on the cell type, the cell suspension needs to be routed into one or more daughter cell culture vessels with a specific split. Split is defined as the ratio between the combined growth surface of the original cell culture vessel(s) and the new surface area of the daughter cell culture vessel(s).

The system achieves this by following up on dissociation steps and performing the following actions:
1) The cell suspension is moved to a mixing vessel that allows agitation of the cell suspension in order to keep cells suspended within the reagents.
2) As the dissociation reagents are often toxic to anchorage-dependent cells, these reagents need to be neutralized while the cells are in suspension to prevent undesired cell death. The liquid handling system automatically adds a pre-warmed cocktail of reagents to the mixing vessel prior to the cell suspension being moved to the mixing vessel to neutralise the dissociation reagents and help the suspended anchorage-dependent cells survive until they can be attached to a new cell culture vessel. The reagents also dilute the cell suspension to desired densities ensuring an appropriate split is achieved in the seeding stage.
3) The mixer function is activated and the fluids are mixed for a period of several minutes to ensure homogeneous cell suspension and mixing of any additional reagents added to the cell suspension. Some other embodiment of the system could also use other means of deactivating dissociation reagents, these could include but are not limited to dilution and decay.
4) A homogenous cell suspension fluid is then transferred to new cell culture vessels of a larger size using a specific split ratio.

Harvesting

When the final passage of a production run is conducted, after the final cell culture vessel(s) in a system have reached confluence, the cells are then dissociated and split to desired densities to form a final product cell suspension. Such suspension is then ready for harvesting. Harvesting is defined as the movement of a final product cell suspension to an additional subsystem within the instrument, or to an additional instrument or external system where the cell suspension is packaged as a final product or intermediate reagent in subsequent manufacturing processes, or manipulated into an additional cell culture vessel or manufacturing system.

Seeding

This is the process of partially filling one or more new or daughter cell culture vessels with a cell suspension, evenly distributing the fluid and cells throughout the culture vessel, and allowing them to adhere to the growth surface of the cell culture vessel(s). This is usually accomplished by hand using a pipette or serological pipette to fill the vessel, and then placing it in a standard incubator to allow the cells to adhere.

The system achieves this step by using a positive displacement pump, multi-axis rotation, and sensors to detect the inclination of the culture vessel.
1) New flasks to which the cells are seeded are covered with a solubilized basement membrane matrix (e.g., Matrigel™). The solubilized basement membrane matrix helps the cells to adhere to the flask, but needs to be removed prior to the cell seeding. Therefore, the first step in seeding is always a removal of solubilized basement membrane matrix from the new culture vessels. Some embodiments of the system could use other matrices, besides Matrigel™
2) Cell suspension is pumped into the culture vessel. The culture vessel is then rocked in a swirling motion using the multi axis gimbal system to ensure that all parts of the vessel are wetted out, and the cell suspension is homogeneously deposited.
3) The culture vessel is subsequently leveled accurately by using sensors, such as a level sensor, to monitor the vessel inclination, and then adjusting the position in the X and Y axis using the multi axis gimbal until the vessel is precisely leveled. This allows the cells to be re-seeded homogeneously.
4) The culture vessel is left in the leveled state while inside a cell culture incubator, which maintains the surrounding environment at optimal temperature conditions.

5) To ensure appropriate growth conditions, the culture medium is changed on each day, without the addition of any dissociation or neutralising reagents.
6) When the confluence is reached again, the cells can be dissociated and split again, moving them into an even larger volume tissue culture vessel or if it is the last stage of the production, the harvesting process is initiated instead.

Figure 29:
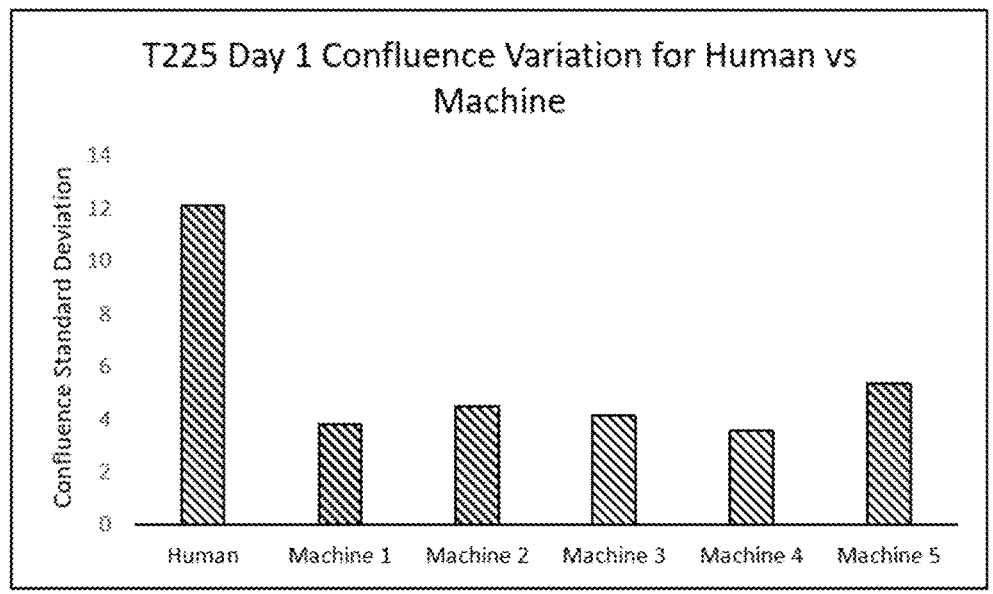
FIG. 29 is a graphical representation showing that the integrated fluid exchange with the multi-axis system ("machine") can perform passaging and growth of adherent cells equivalent to, and in many instances superior to, a skilled operator ("human") performing manual processes.

The system has advantages over current manual processes because, the system shows:
1) More uniform and repeatable mixing of the fluid in the growth vessels.
2) Greater leveling of the culture vessels, leading to a more homogeneous distribution of cells adhered to the vessel. This increases the potential number of cells harvested because cells reach confluence at the same time. The data in the FIG. 29 shows that the confluence achieved within the system is more uniform across the whole flask than in the manual cell culture. These results were based on cell seeding of induced pluripotent stem cells (iPSCs) in commercially available T225 cell culture flask(s). The average confluence is determined for each segment of a flask, divided into 30 equal segments. The Y axis is the standard deviation of the 30 segments relative to the average confluence. The vessels were manually handled and leveled (left bar, marked "human") and the system was used for the leveling, where the results using the system are shown by the other bars.

For a given angle of tilt of the growth surface, increasing the width and length of growth cartridges increases the inhomogeneity of cell seeding because the difference in fluid depth between opposite sides of the vessel increases as the distance between them increases. Therefore, more cells will be seeded where the fluid depth is greater. Table 2 shows the relationship between tilt angle and fluid depth differences for a range of flask sizes. It is clear that even a 0.5° tilt produces a significant unevenness in fluid depth, and therefore the cell seeding distribution for a T225 flask is greater. A 0.5° tilt, or greater, would be easy to unintentionally produce when manually culturing cells by placing the vessels on an unlevel incubator shelf, or by incorrectly stacking vessels.

TABLE 2 tilt angle sensitivity in different flask sizes

| 2 mm Nominal Fill Depth | Ratio of Largest to Smallest Fluid Depth | | |
| --- | --- | --- | --- |
| | 0.5° | 1° | 2° |
| T25 (70 mm Length) | 1.04 | 1.09 | 1.19 |
| T75 (120 mm Length) | 1.71 | 3.20 | One side dry |
| T225 (200 mm Length) | 2.55 | 14.72 | One side dry |

Figure 30:
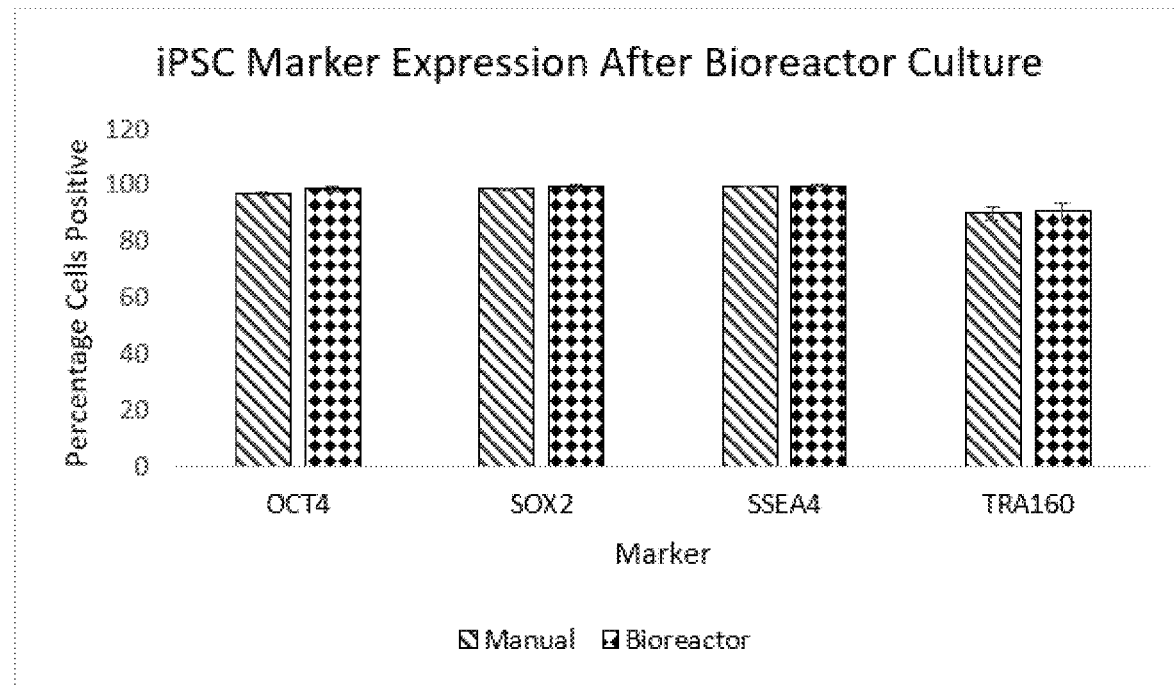
FIG. 30 is a graphical representation showing that pluripotency marker expression in induced pluripotent stem cells (iPSCs) after both manual and automated ("Bioreactor") cell culture with the automated system of the invention, is nearly the same, indicating that both the manual control and automated cell culture using the system of the invention were able to produce iPSCs that maintained a state of pluripotency, a key quality attribute when culturing or manufacturing iPSCs.

FIG. 30 shows data from iPSC cells taken from both the system (bioreactor) and human (manually processed) cell culture vessels from the same experimental setup, where the cells were analyzed using flow cytometry to measure for the expressions of cell surface markers-SSEA4, OCT4, SOX2 and TRA160—which indicate that the iPSCs were still in fact pluripotent. The cells from both the automated system run and the human control run were almost identical, indicating that the automated passaging conducted in the system was able to produce cells of the same quality as a manual operator (which is the current gold-standard for passaging and producing pluripotent stem cells).

This invention could also be part of a wider cell culture automation setup which may include additional fluid distribution networks and pumps, reagent storage, mixing chambers, metabolic sensors, and computer control. Metabolic sensors could be used either directly in the cell culture vessels, or within a centralised sensing unit to decide when fluid processing steps need to be taken. Therefore, the whole process of cell culture, not just the process step of passaging, could be automated because sensors can determine when cell culture steps need to take place (e.g. feeding, passaging, harvest), and the fluid manifold can route fresh or waste reagents into/out of growth vessels as necessary to maintain the cell cultures in an optimal state.

Thus the development of novel automated cell culture vessel handling and cartridge-based fluid exchange systems and their integration into a single instrument is necessary to support the scaled adherent cell manufacturing workflows, including passaging, needed to meet industry demand.

Such an innovation would improve the efficiency and reliability of manufacturing processes, increase product safety and ultimately drive large reductions in production costs by reducing the number of expensive instruments, human labor and floorspace needed to achieve scaled manufacture of adherent cell-based products and therapies.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A system for automating passaging of anchorage dependent or adherent living cells, including adherent mammalian cells, comprising:
   a series of vessels each held within a housing;
   a fluid distribution cartridge having a front and a rear section opposing each other and having a flexible membrane between the front and rear sections, the front section having a series of fluid channels each extending along a surface of the front section opposing the rear section, and said surface of the front section also having a series of recessions in said surface where each said recession intersects a fluid channel and extends more deeply into the front section than does the fluid channel it intersects, and wherein the surface of the rear section opposing each said recession accesses a source of pressurized air, and wherein the air pressure from the source is sufficient to force the flexible membrane into the recessions so as to block the associated fluid channel, and release of air pressure or negative pressure allows the flexible membrane to move back to a neutral position where the fluid channels are open;
   each fluid channel has a junction in it, wherein the junction has an entrance, an exit and a bend at its mid-point such that the fluid channel is directed away from the flexible membrane from the entrance to the mid-point, and the fluid channel is directed towards the flexible membrane from the mid-point to the exit, whereby the flexible membrane occludes and seals the entrance and prevent airflow past the junction when the air pressure from the source is sufficient to block the fluid channels;

the cartridge having a plurality of zones, wherein the fluid channels in at least a first zone of the cartridge are connected with at least one of the series of vessels, and wherein the vessels contain cells or cell solutions, and a first frame rests on a surface and a second frame is attached with the first frame such that the second frame can tilt on a first axis with respect to the first frame, and the housing is attached to the second frame such that the housing can tilt on a second axis with respect to the second frame, and wherein the second axis is orthogonal to the first axis;

a sensor indicating the degree of tilt of the movable frames and the housing, and said sensor providing feedback to an actuator so as to cause the housing to be levelled or tilted to a desired angle in either axis;

the fluid channels in a second zone of the cartridge are connected to either reagent receptacles or cell receptacles, and said fluid channels in said second zone connect with said channels in the first zone; and a microcontroller that controls selective blocking and opening of the fluid channels by controlling the pressurized air to move the flexible membrane, and the sensor and actuator controls the movement of the frames and housing, such that fluid and cellular transfer between a vessel held in the housing and a reagent receptacle or a cell receptacle along the fluid channels in the first and second zones can be controlled, together with controlling the movement and positioning of the housing.

2. The system of claim 1 further including tubing connecting the vessels to the fluid distribution cartridge and tubing connecting the fluid distribution cartridge to the reagent receptacle or the cell receptacle.

3. The system of claim 1 wherein the recessions are hemispheric-shaped.

4. The system of claim 1 wherein the bend at the junction mid-point is a right angle.

5. The system of claim 1 wherein the pumping is performed by a built-in diaphragm pump within the cartridge.

6. The system of claim 5 wherein the pumping is performed by forcing the flexible membrane to block and open the fluid channels using the pressurized air applied in a timed sequence.

7. The system of claim 5 wherein the pumping is performed by a peristaltic pump.

8. The system of claim 1 further including a motor which allows the housing to be oscillated or moved in a third axis, which is orthogonal to the first and second axes.

9. The system of claim 1 wherein the sensor is an inclination sensor which indicates the angular positioning of the housing in at least the first and second axes.

10. The system of claim 1 wherein the cartridge is connected to a non-disposable docking station to which pneumatic tubing is connected.

11. The system of claim 1 wherein the cartridge includes fluidic connectors attaching to fluidic ports which access the fluidic channels in the front section of the cartridge.

12. The system of claim 1 wherein the cartridge includes pneumatic connectors attaching to pneumatic ports which access the membrane on the rear side of the cartridge.

13. The system of claim 1 wherein the vessel is fixed inside the housing.

14. The system of claim 1 wherein the system includes more than one vessel and the cartridge has connections such that fluid can be transferred among vessels.

15. The system of claim 1 further including at least one additional cartridge through which fluid can be transferred.

16. The system of claim 1 further including more than one receptacle, wherein fluid can be transferred to or from the receptacles.

17. The system of claim 1, wherein the fluid distribution cartridge includes several zones of multiple fluid channels fluids can be transferred independently within a zone and fluid can be transferred to other zones.

18. The system of claim 17, where the number of connections to each zone can be expanded by adding additional fluid distribution cartridges.

19. The system of claim 1, wherein the first frame is in has two legs each formed by a U-shaped support, with two vertical arms joined at their tips by two mid-section pieces and the second frame is formed of four supports joined at right angles at their tips, and the first frame and the second frame are attached to each other with at least one pin extending through each of the two mid-section pieces of the first frame and through two of the supports of the second frame.

* * * * *